United States Patent
Subhash

(10) Patent No.: US 12,268,516 B2
(45) Date of Patent: Apr. 8, 2025

(54) SYSTEM AND METHOD FOR ORAL HEALTH MONITORING USING ELECTRICAL IMPEDANCE TOMOGRAPHY

(71) Applicant: Colgate-Palmolive Company, New York, NY (US)

(72) Inventor: Hrebesh Molly Subhash, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 207 days.

(21) Appl. No.: 16/699,809

(22) Filed: Dec. 2, 2019

(65) Prior Publication Data

US 2020/0187850 A1    Jun. 18, 2020

Related U.S. Application Data

(60) Provisional application No. 62/779,584, filed on Dec. 14, 2018.

(51) Int. Cl.
*A61B 5/00* (2006.01)
*A61B 5/0536* (2021.01)

(52) U.S. Cl.
CPC .......... *A61B 5/4552* (2013.01); *A61B 5/0536* (2013.01); *A61B 5/6847* (2013.01); *A61B 2562/046* (2013.01); *A61B 2562/164* (2013.01)

(58) Field of Classification Search
CPC ... A61B 5/4542; A61B 5/4547; A61B 5/4552; A61B 5/0534; A61B 5/0536;
(Continued)

(56) References Cited

U.S. PATENT DOCUMENTS 5,490,520 A * 2/1996 Schaefer ............... A61F 5/566
128/848
5,617,876 A    4/1997 van Duyl
(Continued)

FOREIGN PATENT DOCUMENTS

CN    102946797    2/2013
CN    104812299    7/2015
(Continued)

OTHER PUBLICATIONS

English-language machine translation of WO 2018/011241, pp. 1-11, 2018 (Year: 2018).*
(Continued)

*Primary Examiner* — Daniel L Cerioni
*Assistant Examiner* — Om Patel

(57) ABSTRACT

A system, instrumentality, and method for performing an oral care evaluation of a user via electrical impedance tomography (EIT). For example, a system may include an oral care device having a first member housing a first electrode. The first electrode may be configured to transmit a first signal through a gingiva of a user to cause an altered first signal. The oral care device may have a second member housing a second electrode. The second electrode may be configured to receive the altered first signal. The system may be configured to generate an electrical impedance tomography (EIT) profile of the gingiva of the user, for example, based on data indicative of the first signal and the altered first signal. An oral health characteristic of the user may be determined based on the EIT profile of the gingiva of the user.

9 Claims, 16 Drawing Sheets

(58) Field of Classification Search
CPC ............... A61B 5/6846; A61B 5/6847; A61B 2562/046; A61B 2562/164; A61B 5/682; A61B 5/0531
See application file for complete search history.

(56) References Cited

U.S. PATENT DOCUMENTS

| | | | |
|---|---|---|---|
| 6,236,886 B1 | 5/2001 | Cherepenin et al. | |
| 6,584,348 B2 | 6/2003 | Glukhovsky | |
| 6,690,181 B1 | 2/2004 | Dowdeswell et al. | |
| 8,326,413 B1 | 12/2012 | McClain et al. | |
| 8,359,179 B2 * | 1/2013 | Bruce | A61B 5/0534 702/108 |
| 8,660,669 B2 | 2/2014 | Nemeh et al. | |
| 9,111,372 B2 | 8/2015 | Ortega et al. | |
| 9,445,742 B2 | 9/2016 | Slizynski et al. | |
| 9,955,918 B2 | 5/2018 | Paris et al. | |
| 10,226,210 B2 | 3/2019 | Abboud et al. | |
| 10,376,210 B2 | 8/2019 | Paris et al. | |
| 10,517,525 B2 | 12/2019 | Yoon et al. | |
| 10,617,502 B2 | 4/2020 | Nemeh et al. | |
| 2001/0051774 A1 | 12/2001 | Littrup et al. | |
| 2006/0004301 A1 | 1/2006 | Kasevich | |
| 2008/0280248 A1 | 11/2008 | Pitts et al. | |
| 2013/0046168 A1 * | 2/2013 | Sui | A61B 8/0891 600/407 |
| 2014/0093832 A1 * | 4/2014 | Nemeh | A61C 19/066 433/1 |
| 2015/0313559 A1 | 11/2015 | Ortega et al. | |
| 2016/0228177 A1 | 8/2016 | Eckhouse et al. | |

FOREIGN PATENT DOCUMENTS

| | | | |
|---|---|---|---|
| CN | 105682606 | 6/2016 | |
| CN | 107518952 | 12/2017 | |
| GB | 2427923 | 1/2007 | |
| RU | 2188576 | 9/2002 | |
| WO | 1992/006634 | 4/1992 | |
| WO | WO-9317615 A1 * | 9/1993 | ......... A61B 5/14542 |
| WO | WO-2006037956 A1 * | 4/2006 | ............. A61B 5/053 |
| WO | WO-2006045607 A1 * | 5/2006 | ............ A61B 5/0031 |
| WO | 2014/110548 | 7/2014 | |
| WO | WO-2017218947 A1 * | 12/2017 | ........... A61B 5/0015 |
| WO | WO-2018011241 A1 * | 1/2018 | ............ A61B 5/0534 |

OTHER PUBLICATIONS

Daschner et al., 2016, "Suitability of electrical impedance tomography for the detection of dental pulp inflammation," Proceedings of the 11th International Conference on Electromagnetic Wave Interaction with Water and Moist Substances.

International Search Report and the Written Opinion of the International Searching Authority issued in International Application PCT/US2019/063911 mailed Feb. 3, 2020.

Zargari et al., 2015, "Electrical impedance tomography system to circumstances recognition of tissue in an experimental phantom: Tooth a case study," Biological Science 5(8S):594-603.

Li Zhangyong, "Bioimpedance technology and gastric motility assessment," Chongqing University Press, published Mar. 2011, 1st edition, p. 19.

Yang, Zhendong, "Practical Disease Diagnosis and Treatment," Chongqing University Press, published Jan. 2001, 1st edition, p. 1077.

* cited by examiner

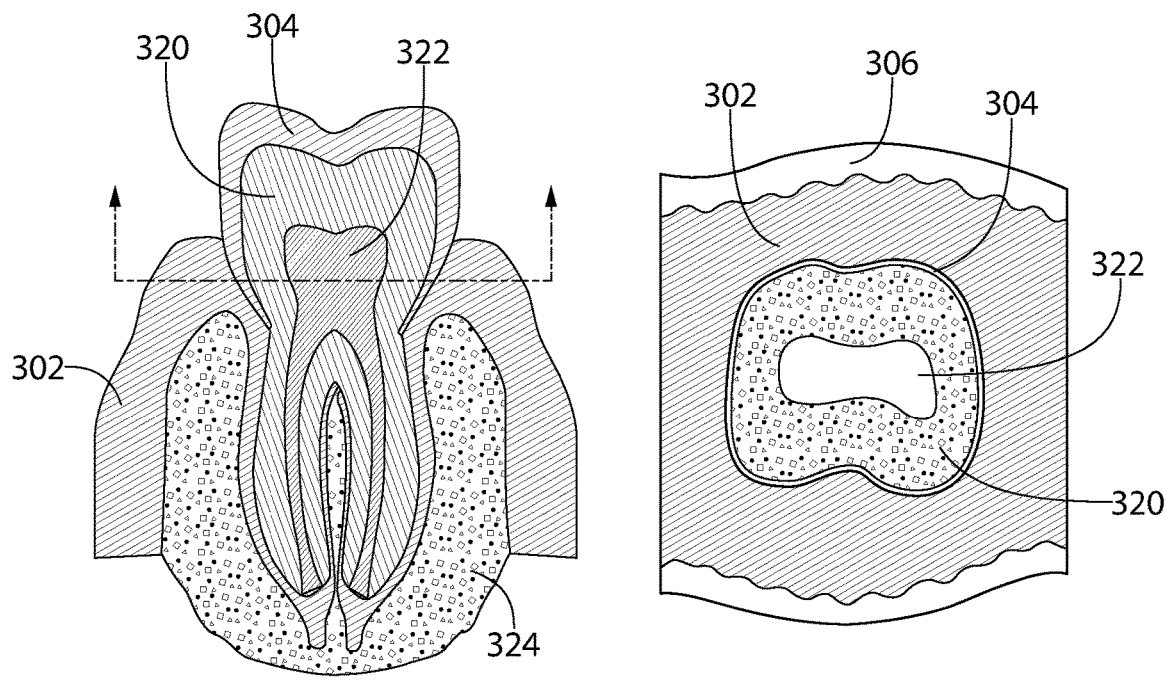
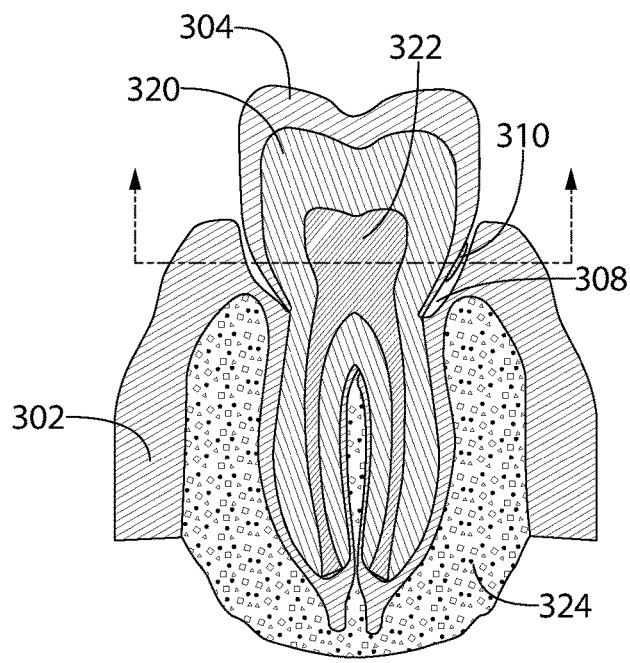
FIG. 3A  FIG. 3B
FIG. 3C  FIG. 3D

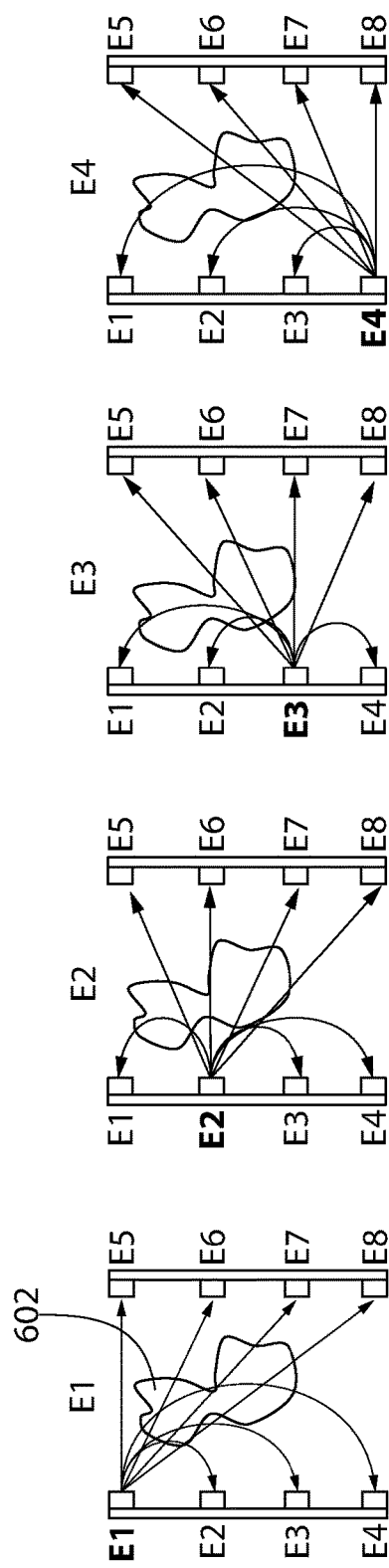
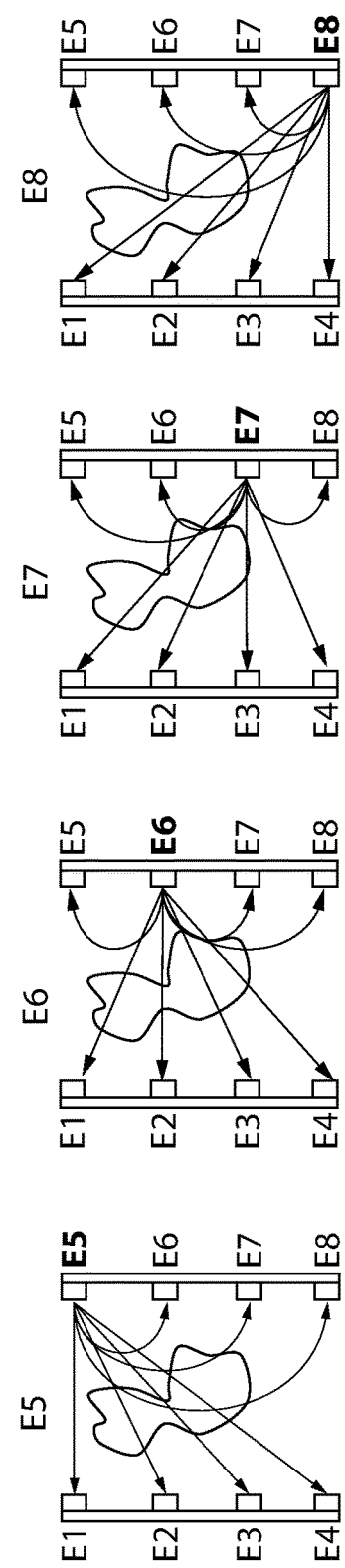
FIG. 6A FIG. 6B FIG. 6C FIG. 6D
FIG. 6E FIG. 6F FIG. 6G FIG. 6H

SYSTEM AND METHOD FOR ORAL HEALTH MONITORING USING ELECTRICAL IMPEDANCE TOMOGRAPHY

CROSS-REFERENCE TO RELATED APPLICATIONS

The present application claims priority to U.S. Provisional Patent Application Ser. No. 62/779,584, filed on Dec. 14, 2018, the entirety of which is incorporated herein by reference.

BACKGROUND

Oral health problems can take many forms, such as tooth decay, oral cancer, periodontal disease, and bad breath. As an example, periodontal disease is often caused by certain bacterial species in the mouth that interact with proteins present in saliva to form a film, known as plaque, that coats the teeth. If this biofilm build-up progresses, the acid produced by the bacteria can attack the teeth resulting in tooth decay. The plaque may also attack the soft gum tissue of the mouth leading to gingivitis, which affects the gingiva, or periodontitis, which may affect the soft tissue and bone supporting the teeth.

Gingivitis is an inflammation of the gingiva characterized by redness, swelling, bleeding, and sensitivity. These changes result from an accumulation of biofilm along the gingival margins and the immune system's inflammatory response to the release of destructive bacterial byproducts. Investigations of the pathogenesis of periodontitis focus on the initiation and progression of the disease process, such as the progression from health to gingivitis, from acute to chronic inflammation, and from gingivitis to periodontitis. Gingivitis results in increased vascularity and morphological change in the vascular and tissue architecture.

Monitoring and assessment of local inflammatory changes such as tissue morphology, vascularity, crevicular fluid buildup, early detection of periodontal pocket, gum volume change during disease progression and response to therapy is crucial for understanding the pathophysiology. The early stages of gingivitis are reversible with thorough brushing and flossing. Without adequate oral hygiene, however, chronic infections and periodontitis can develop.

BRIEF SUMMARY

Exemplary embodiments according to the present disclosure are directed to an oral care evaluation system, device, and/or method which may be used to evaluate an oral care characteristic of a user via, for example, electrical impedance tomography (EIT). The oral care evaluation system, device, and/or method may be related to a point of care system, device, and/or method. In other examples, the oral care evaluation system, device, and/or method may be related to a personal care monitoring/tracking system, device, and/or method, or another care monitoring/tracking system, device, and/or method.

In an aspect, a system may include an oral care device. The oral care device may have a first member housing a first electrode. The first electrode may transmit a first signal through an oral cavity (e.g., a gingiva) of a user, for example, to cause an altered first signal. The system may have a second member housing a second electrode. The second electrode may receive a signal, such as the altered first signal. The system may receive (e.g., from the oral care device) data indicative of the first signal and the altered first signal. The system may generate an electrical impedance tomography (EIT) profile of the gingiva of the user, for example, based on the data indicative of the first signal and the altered first signal.

An oral health characteristic of the user may be determined, for example, based on the EIT profile of the gingiva of the user. The oral health characteristic of the user may be determined based on a single EIT profile of the gingiva of the user. For example, it may be determined if the gingiva of the user is normal or abnormal based on a single EIT profile of the user. The oral health characteristic may be determined based on more than one EIT profile (e.g., based on a comparison of the user's EIT profile with previously observed/generated EIT profiles), such as via a pool of EIT profiles. The more than one EIT profile may be EIT profiles of the user, in an example. In other examples, the more than one EIT profile may be EIT profiles of users other than the user. Determining the oral health characteristic of the user may include determining the presence of a periodontal pocket, a gum volume change, a periodontal bone loss, an abnormal connective tissue change, and/or a quantification of a gingival crevicular fluid. The EIT profile of the gingiva of the user may be determined based on a potential difference between the first signal and the altered first signal.

One or more of the first member and the second member may be configured to be positioned upon a mouthpiece. One or more of the first member and the second member may be a flexible membrane. The first member may be configured to be placed upon an anterior portion or a posterior portion of the gingiva of the user. A second member may be configured to be placed upon another one of the anterior portion or the posterior portion of the gingiva. One or more of the first member and second member may house an electrode array.

The system may wirelessly receive the data indicative of the first signal and the altered first signal. The system may include a display device that displays a representation of the EIT profile.

BRIEF DESCRIPTION OF THE DRAWINGS

FIGS. 3A-3D show example views of a user's periodontium in the oral cavity, wherein FIGS. 3A, 3C show cross sectional views of a user's cavity and FIGS. 3B, 3D show top-down views of a user's cavity.

FIGS. 6A-6H show example signal transmissions corresponding to a two-pole (8 electrode) configuration.

DETAILED DESCRIPTION

Figure 1:
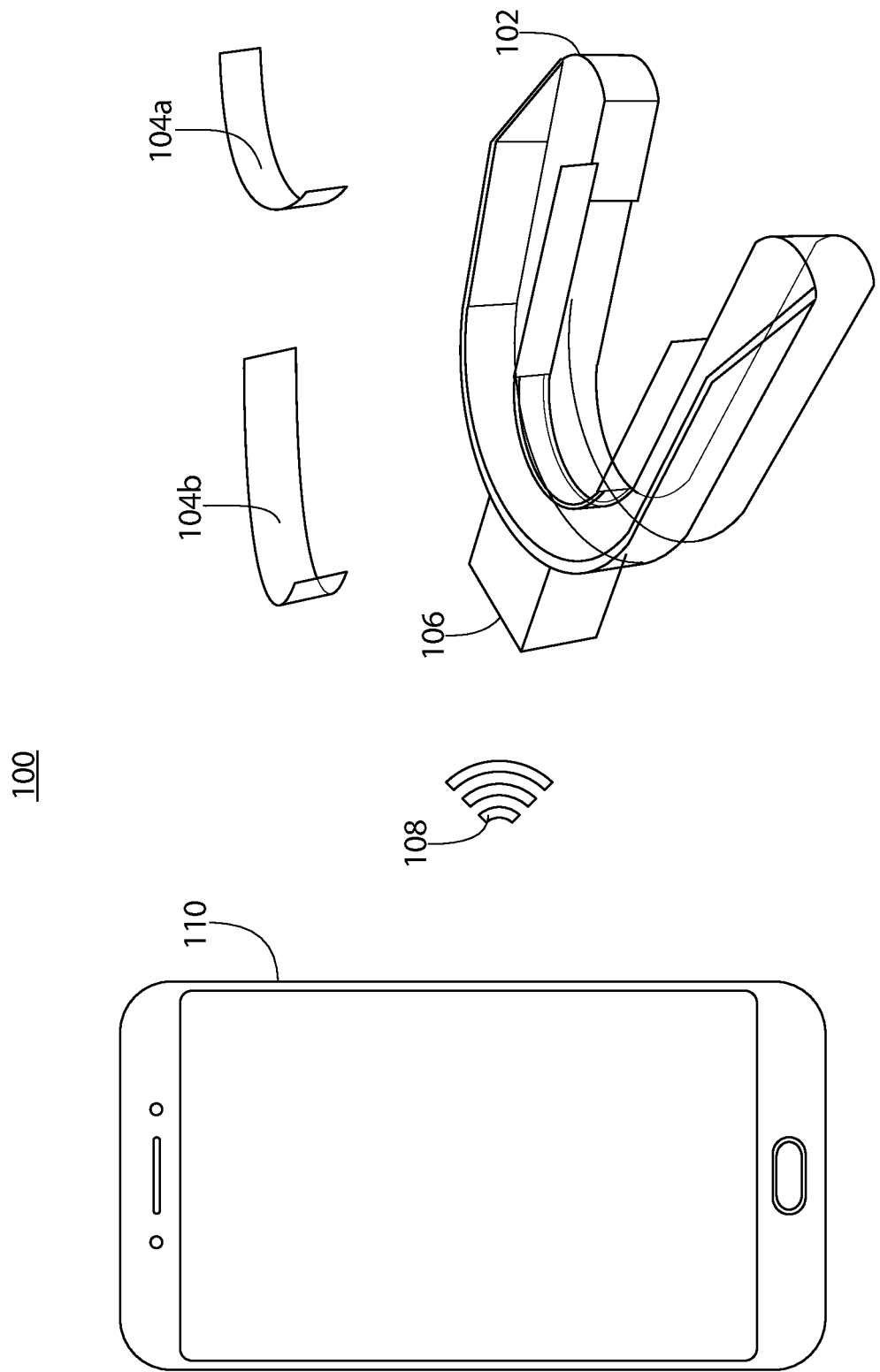
FIG. 1 depicts an example oral care system using electrical impedance tomography (EIT).

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof. The computer programmable processes may be executed on a single processor or on or across multiple processors.

Processors described herein may be any central processing unit (CPU), microprocessor, micro-controller, computational, or programmable device or circuit configured for executing computer program instructions (e.g. code). Various processors may be embodied in computer and/or server hardware and/or computing device of any suitable type (e.g. desktop, laptop, notebook, tablet, cellular phone, smart phone, PDA, etc.) and may include ancillary components used to form a functional data processing device including without limitation a bus, software and data storage such as volatile and non-volatile memory, input/output devices, a display screen, graphical user interfaces (GUIs), removable data storage, and wired and/or wireless communication interface devices including Wi-Fi, Bluetooth, LAN, etc.

Computer-executable instructions or programs (e.g. software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to hereinafter as a "programmable device," or a "device" for short, and multiple programmable devices in mutual communication may be referred to as a "programmable system."

It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Turning in detail to the drawings, FIG. 1 illustrates an example oral care system 100 for monitoring and/or determining an oral health characteristic of a user. For example, the oral care system 100 may be used to monitor and/or determine the gum, tooth, and/or bone health within the oral cavity of a user via electrical impedance tomography (EIT), such as miniature EIT. In one or more examples system 100 may be a point of care system, sometimes referred to as a point of care testing (POCT) system. For example, system 100 may be used for and/or applied at a primary care office at the time and place of a user's (e.g., patient's) care. In other examples, the oral care evaluation system, device, and/or method may be related to a personal care monitoring/tracking system, device, and/or method. In such examples, system 100 may be used for and/or applied by a consumer (e.g., at the home of the consumer) to monitor and/or track the oral health (e.g., gingival health) of the consumer.

EIT is a technique of obtaining a tomographic image (e.g., for medical diagnostics) based on the use of an electric current. EIT, as described herein, may be used as a sensitive and/or accurate diagnostic tool that may provide high resolution structural, functional, and spectroscopic information for the early detection of diseases in the oral cavity. An example EIT technique may include placing electrodes (e.g., a series of contact electrodes) on the surface of a user, such as within the oral cavity (e.g., the gingiva) of the user.

One or more electrodes may transmit one or more signals within the oral cavity (e.g., through the gingiva) of the user. Sending the signals through the gingiva of the user may cause a signal to be generated. The generated signal may be based on the transmitted signal. For example, the generated signal may be an altered transmitted signal.

The electrodes may form one or more electrode arrays. The electrode arrays may transmit array signals, for example, within the oral cavity (e.g., through the gingiva) of the user. Sending the array of signals through the gingiva of the user may cause a signal (e.g., an array of signals) to be generated. The generated array of signals may be based on the transmitted array of signals. For example, the generated array of signals may be one or more of the altered array of signals that were transmitted.

In an example, a source of electric current may be connected (e.g., connected sequentially) to pairs of electrodes. Measurements of potential differences (voltages) between the pairs of electrodes may be performed. The potential differences may exist, for example, due to the current flow through the user (e.g., through the user's gingiva, teeth, bone, tissue, etc.).

Reference values of potential differences (voltages) may be determined based on the assumption of homogeneity of electrical conductivity of the user (e.g., gingiva of the user). Reference values of potential differences (voltages) may be determined by measuring one or more potential differences of a user, for example, at different times.

A tomographic image may be constructed, for example, from the spatial conductivity distribution of the user and/or from changes in the conductivity between two measurements (e.g., using back projection or the relative differences of measured and reference voltages along equipotential lines of an electric field). The electrical conductivity of biological tissue within the oral cavity of a user (e.g., within the gingiva of a user) may depend on the tissue's physiological properties. The conductivity distribution of the tissue may be used to create images of the tissue, for example, images of the hard tissue (e.g., bones, teeth, etc.) and/or the soft tissue (e.g., gingiva).

As described herein, system 100 may be used to monitor and/or determine the tissue morphology (e.g., internal tissue morphology) and/or composition of a user's oral cavity (e.g., gingiva, tooth, bone, etc.) via EIT. Electrodes may be placed within the oral cavity of a user to monitor and/or determine the tissue morphology and/or composition of a user's oral cavity (e.g., gingiva, tooth, bone, etc.) via EIT.

For example, as provided in the example shown on FIG. 1, system 100 may include a mouthpiece 102 for insertion into a user's oral cavity. The mouthpiece 102 may be formed to fit a particular user, or, in other examples, the mouthpiece may be sized to fit a variety of users. The mouthpiece may be formed of one or more of a variety of materials, including a thermoplastic, a thermo-polymer, etc. A single mouthpiece 102 may be configured to be placed upon both the upper and lower portion (e.g., gingiva) of a user. In other examples, a mouthpiece 102 may be configured to be placed upon the top portion of a user's oral cavity, and another mouthpiece 102 may be configured to be placed upon the bottom portion of a user's oral cavity.

Mouthpiece 102 may include one or more devices. One or more components and/or devices may be coupled to the mouthpiece 102. In an example, mouthpiece 102 may be configured to include one or more electrodes. The mouthpiece 102 may include one or more electrodes, for example, in which the electrodes are directly attached (e.g., attached via an adhesive) to the mouthpiece 102. The mouthpiece 102 may be configured to receive one or more mediums having one or more electrodes. For example, the mouthpiece may be configured to receive one or more members 104a, 104b. The one or more members 104a, 104b may be detachably coupled to the mouthpiece 102, or the members 104a, 104b may be permanently coupled to the mouthpiece, for example, via an adhesive. In examples, the mouthpiece 102 may include a slot for receiving the one or more members 104a, 104b. In other examples, electrodes may be directly attached to the oral cavity of a user, for example, without the use of a mouthpiece or one or more of the members 104a, 104b.

One or more of the members 104a, 104b may house one or more electrodes or electrode arrays. For example, the electrodes may be attached (e.g., permanently attached or detachably attached) to the members 104a, 104b via one or more methods of attaching electrodes. The electrodes may be attached to the members 104a, 104b in one or more configurations. For example, the electrodes (e.g., electrode arrays) may be printed upon one or more of the members 104a, 104b in one or more sequences. As provided herein, the members 104a, 104b may be housed by the mouthpiece 102. In other examples, the members 104a, 104b may be positioned about the oral cavity of the user without use of the mouthpiece 102. For example, the members 104a, 104b may be positioned about the oral cavity of the user by directly attaching (e.g., via an adhesive) the members 104a, 104b to the gingiva of a user, by the user assisting with holding the members 104a, 104b to the gingiva of the user, and the like.

The members 104a, 104b may be formed of one or more different materials and may be formed in one or more different configurations. For example, the members 104a, 104b may be formed so as to be flexible, as shown on FIG. 1. In other examples, one or more of the members 104a, 104b may be formed as to be rigid or may be formed as to be a mix of being rigid and flexible. The members 104a, 104b may be formed as strips, as shown in FIG. 1, or the members 104a, 104b may be formed in different form factors, such as to fit a particular user, to receive the best results, etc.

Mouthpiece 102 may include a transmitting device, such as example transmitting device 106. Mouthpiece 102 may be coupled to the transmitting device 106 and/or the transmitting device 106 may be formed within the mouthpiece 102. Transmitting device 106 may be configured to transmit via one or more communications, such as via example communication 108. Communication 108 may be a wired communication, a wireless communication (e.g., Bluetooth, Wi-Fi, etc.), or a combination of a wired and wireless communications. The transmitting device 106 may transmit one or more signals, including one or more types of information, to one or more devices, such as a processing device 110. Transmitting device 106 may transmit one or more signals, including one or more types of information, to a server (e.g., the cloud). Transmitting device 106 may transmit one or more types of information, such as the EIT profile of a user, an oral healthcare characteristic of the user, a signal sent and/or received by one or more electrodes, etc. The one or more types of information may be sent (e.g., sent from mouthpiece 102) for storage.

Mouthpiece 102 may include a signal processing circuit, as described herein. Mouthpiece 102 may include a processor. The signal processing circuit may include one or more processors. Mouthpiece 102 may be coupled to the signal processing circuit and/or the signal processing circuit may be formed within the mouthpiece 102. Mouthpiece 102 may be configured (e.g., via one or more signal processing circuits) to process information, such as the information sent and/or received by the electrodes. In examples, the signal processing circuit may also, or alternatively, perform as a transmitting device.

For example, mouthpiece 102 may process (e.g., pre-process) information before the pre-processed information is sent to an external device (e.g., a computing device, such as a mobile phone and/or a server, such as the cloud) via the transmitting device 106. For example, mouthpiece 102 may serve as an Internet of Things (IoT) device. In such an example, mouthpiece 102 may send information (e.g., pre-processed information) to a cloud-based server for further processing, data extraction, and the like. Mouthpiece 102 may generate an EIT profile of a user and/or determine a healthcare characteristic of a user based on the signals sent and/or received by one or more electrodes.

System 100 may include one or more processing devices 110. Processing device 100 may be used to process data and/or to store data. In an example, processing device 110 may be coupled to the mouthpiece 102. In other examples, processing device 102 may be external to the mouthpiece 102. Although processing device 110 on FIG. 1 is shown as a mobile phone, processing device 110 may be any device that can be used for receiving, processing, storing, and/or sending information. For example, processing device 110 may be a computer, laptop, tablet, mobile phone, etc. Processing device 110 may be a server, such as a cloud-based server. Processing device 110 may include one or more processors for the device's general processing purposes. The processors may be, for example, an ARM-based system on chip (SoC), or an Exynos SoC. These processors may include a central processing unit (CPU), input/output ports, and secondary storage.

Processing device 110 may perform calculations based on the information received from transmitting device 106. For example, processing device may be used to display the EIT profile of the oral cavity of the user and/or to perform the calculations for generating an EIT profile of the user, etc. Processing device 110 may transmit to one or more other devices (e.g., another processing device 110, a server, the cloud, etc.). The processing device 110 may transmit to the one more other devices using the same, or different, communication (e.g., communication 108) as the processing device 110 uses to receive the information from the transmitting device 106. For example, communication may be a wired communication, a wireless communication (e.g., Bluetooth, Wi-Fi, etc.), or a combination of a wired and wireless communications. Processing device 110 may transmit one or more types of information, such as the EIT profile of a user, an oral healthcare characteristic of the user, a signal sent and/or received by one or more electrodes, etc. The one or more types of information may be sent (e.g., sent from processing device 110) for storage.

Figure 2A:
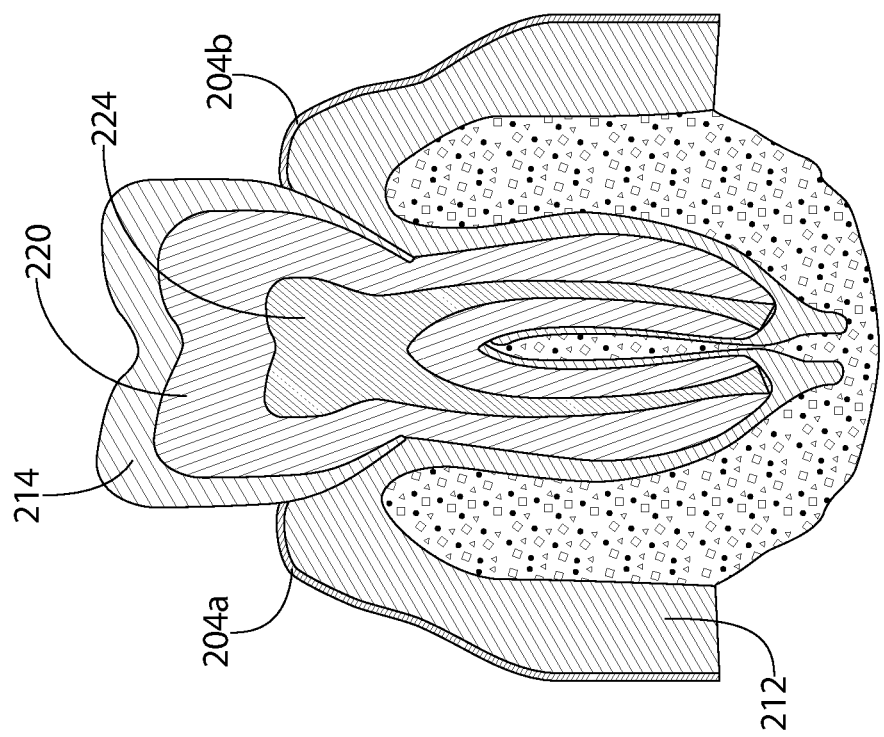
FIG. 2A is a cross-sectional view of periodontium of an example oral cavity of a user.
Figure 2B:
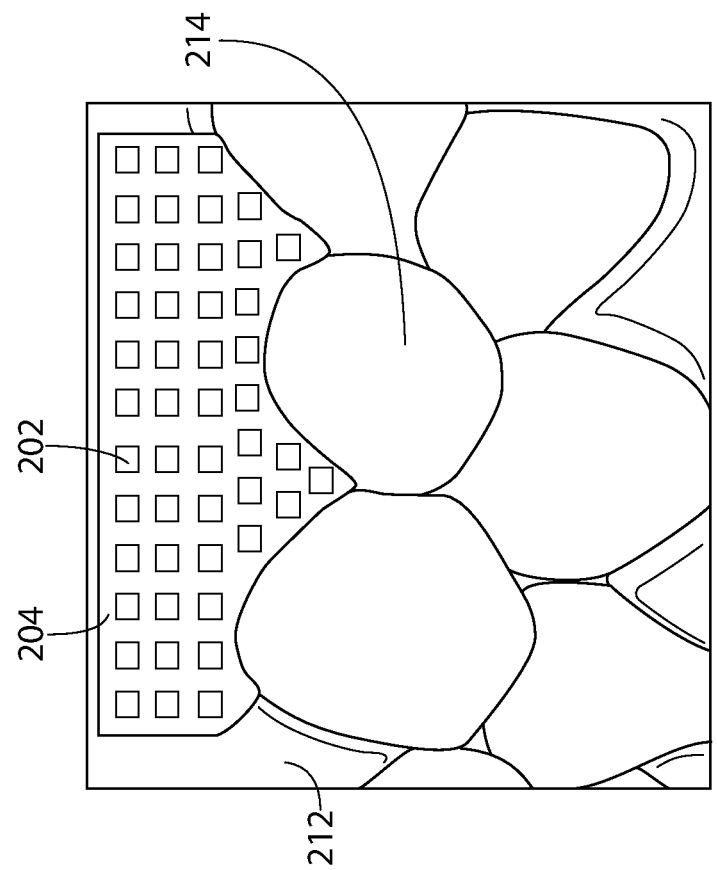
FIG. 2B is a blown-up view of an example placement of a member upon the gingiva of a user.

FIGS. 2A and 2B show example placements of the member(s) 204a, 204b upon the gums of a user.

FIG. 2A is a cross-sectional view of periodontium of an example oral cavity of a user. In particular, FIG. 2A shows the enamel 214, dentin 220, pulp 222, gingiva 212, and bone 224 of an oral cavity of a user. One or more electrodes may be placed within the oral cavity of a user. For example, one or more members may include one or more electrodes (and/or electrode arrays) that may be placed within the oral cavity of a user.

FIG. 2A provides an example placement of members 204a, 2024b upon the gingiva 214 of a user. As an example, member 204a may be placed on the anterior portion of a user's gingiva 212 and/or member 204b may be placed on the posterior portion of a user's gingiva 212. One or more members may be placed within the oral cavity of a user to cover a portion, or the entirety, of a user's gingiva.

As shown on FIG. 2B, member 204 may include one or more electrodes 202. The placement of the electrodes 202 as shown on FIG. 2B is for illustration purposes only. For example, the number of the electrodes 202 on the member 204, placement of the electrodes 202, and/or the formation of the member 204 may differ in one or more other examples. Further, although a single member is shown on FIG. 2B, in other examples there may be additional, different, or similar, members placed upon one or more portions of a user's gingiva.

As described herein, electrodes (e.g., electrode 202) may be used to send and/or receive a signal (e.g., an electrical signal) within the oral cavity of a user, for example, to monitor and/or determine the oral health of the user. The electrodes may be placed in an array (e.g., electrode array). The electrodes may be fabricated using a circuit board, such as a flexible printed circuit board. The electrodes may be plated with a conductive material, such as with gold. One or more of the members housing the electrodes may be formed in any shape, including but not limited to the shape of a user's gingiva. The electrodes may be formed upon the member using any known forming technique (e.g., inject printing) using a flexible plastic substrate multiplexed micro-electrode array.

Electrical impedance tomography (EIT) may be used to monitor and/or determine whether a user has gingivitis, periodontitis, or the like. A tomographic image of the oral cavity (e.g., the gingiva) of a user may be generated based on a signal (e.g., an electric signal, such as an electric current) sent by an electrode and/or a signal (e.g., an electric signal, such as a voltage) received by another electrode. The received signal may be an altered version of the sent signal, and/or the received signal may be a signal based on something other than the sent signal.

The signal (e.g., electrical signal) received by an electrode may be based on the electrical signal sent by an electrode (e.g., another electrode). The electrical signals may be sent and/or received in many different configurations. For example, an array (e.g., a series) of electrodes may be placed on the surface of a user's gingiva. Electric current may be connected (e.g., connected sequentially) to pairs of the electrodes. Measurements of potential differences (e.g., voltages) between the pairs of electrodes may be performed. The potential differences may arise due to the current flowing through the gingiva. The potential differences may be used to generate an EIT profile, as described herein.

In an example, one or more potential differences may be compared to reference values to determine the oral health (e.g., an oral health characteristic) of a user. The potential differences may be compared to previous measures taken by the same user and/or different users. An image (e.g., a tomographic image) may be generated based on the measured potential differences. The image may be constructed based on a spatial conductivity distribution of the gingiva and/or from changes in the conductivity between two measurements (e.g., the change of conductivity sent from the sending electrode and received from the receiving electrode).

The electrical conductivity of the matter within the oral cavity may depend on the physiological properties of the particular matter within the oral cavity. The conductivity distribution of the particular matter may be used to create images of a user's teeth, bones, soft tissue (e.g., gingiva), or the like.

FIGS. 3A-3D show cross sectional and top-down views of periodontium of a user's oral cavity. In particular, FIG. 3A shows a cross sectional morphology of an example normal gingiva, and FIG. 3B shows a top-down view of the example normal gingiva. FIG. 3C shows a cross sectional morphology of an example abnormal gingiva, and FIG. 3D shows a top-down view of the example abnormal gingiva.

FIGS. 3A, 3B show gingiva 302 of the user, as well as enamel 304, tissue 306, dentin 320, pulp 322, and bone 324 of a user. The top cross-section of FIG. 3A corresponds to the dotted line at the marginal gum area. As can be seen, there is no bone in the top cross-section of FIG. 3A. As further seen in the examples shown on FIGS. 3A, 3B, a normal gingiva may exhibit a firm and resilient consistency.

FIGS. 3C, 3D show gingiva 302 of the user, as well as enamel 304, tissue 306, dentin 320, pulp 322, and bone 324 of a user. FIGS. 3C, 3D further show plaque and tartar 310, and a pocket 308 found within an example oral cavity. As described above for FIG. 3A, the top cross-section of FIG. 3C corresponds to the dotted line at the marginal gum area.

As can be seen on FIGS. 3C, 3D, an abnormal gingiva may exhibit soggy and edematous with leathery consistency. Further, FIGS. 3C, 3D show loss of bone 324, compared to FIGS. 3A, 3B, as well as inflamed tissue 306 (e.g., more water and blood is shown on FIGS. 3C, 3D than in FIGS. 3A, 3B). An abnormal gingiva may show additional characteristics that differ from a normal gingiva. The examples provided herein are for illustration purposes only.

The electrical impedance profile of the gingiva may be defined based on cellular and fluid content, the collagenous nature of lamina propria, as well as other properties. Thus, normal gingiva (FIGS. 3A, 3B) may have an electrical impedance profile that differs from the electrical impedance profile of the abnormal gingiva (FIGS. 3C, 3D).

EIT images may be used to determine whether the gingiva of a user is normal or abnormal, for example, due to the electrical impedance profile differences between normal gingiva and abnormal gingiva. Different characteristics of the electrical impedance profiles may be monitored and/or determined to determine the characteristics of the user's oral health (e.g., gum health). For example, the measurements may be defined according to different frequencies in which the electrical signals were sent, were received, or a combination of the frequencies that were sent and received. The EIT images and/or the EIT profile may be displayed to a user, for example, via a computer, laptop, tablet, smartphone, etc.

Figure 4:
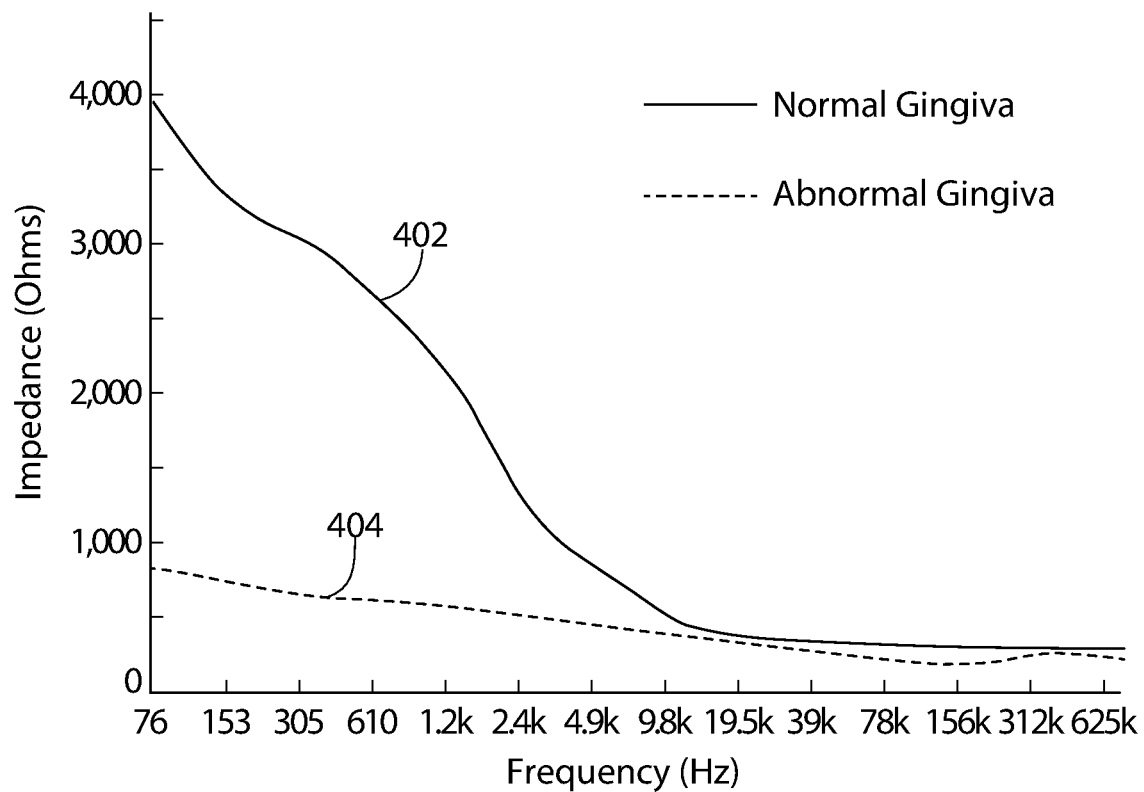
FIG. 4 shows example EIT profiles of normal and abnormal gingiva.

FIG. 4 shows an example EIT profile of a normal gingiva 402 and an example EIT profile of an abnormal gingiva 404. In particular, FIG. 4 shows an example EIT profile of a normal gingiva 402 (e.g., gingiva) and an example EIT profile of an abnormal gingiva 404 (e.g., abnormal gingiva) wherein frequencies of the applied currents are between 10 Hz through 850 kHz. As can be seen on FIG. 4, the EIT profiles of the normal and abnormal gingiva tissue may differ based on the frequencies (e.g., frequencies of the currents applied to the respective gingiva tissue). Based on the EIT profiles provided on FIG. 4, EIT profiles of one or more users may be used to determine and/or monitor the oral health (e.g., gum health) of a user. As shown on FIG. 4, at frequencies between 10 Hz-2.4 KHz, the EIT profile of the applied current may be used to determine the oral health (e.g., gum health) of a user.

As described herein, the oral health characteristic of the user may be determined based on one or more EIT profiles. For example, it may be determined if the gingiva of the user is normal or abnormal based on a single EIT profile of the user. The oral health characteristic may be determined based on more than one EIT profile (e.g., based on a comparison of the user's EIT profile with previously observed/generated EIT profiles), such as via a pool of EIT profiles. The more than one EIT profile may be EIT profiles of the user, in an example. In other examples, the more than one EIT profile may be EIT profiles of users other than the user. Determining the oral health characteristic of the user may include determining the presence of a periodontal pocket, a gum volume change, a periodontal bone loss, an abnormal connective tissue change, and/or a quantification of a gingival crevicular fluid. The EIT profile of the gingiva of the user may be determined based on a potential difference between the first signal and the altered first signal.

Figure 5A:
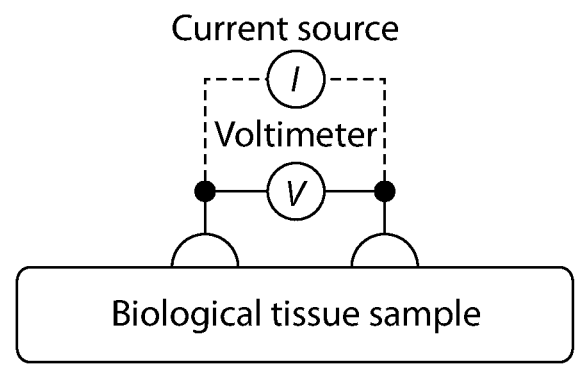
FIGS. 5A, 5B depict example EIT two-pole and four-pole electrode configurations.
Figure 5B:
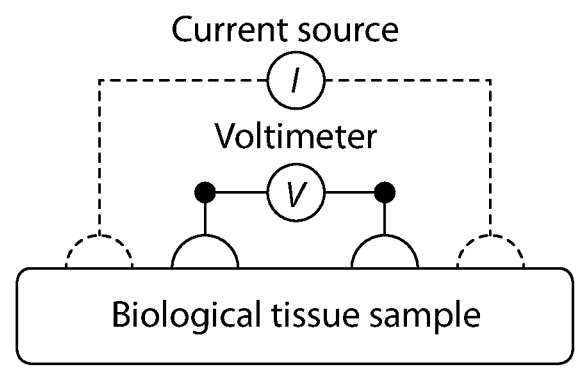

FIGS. 5A, 5B depict example EIT electrode configurations that may be used to determine the oral health of a user. For example, FIGS. 5A, 5B depict example two-pole (FIG. 5A) and four-pole (FIG. 5B) electrode configurations, respectively, that may be used to determine the oral health (e.g., an oral health characteristic) of a user.

Figure 7:
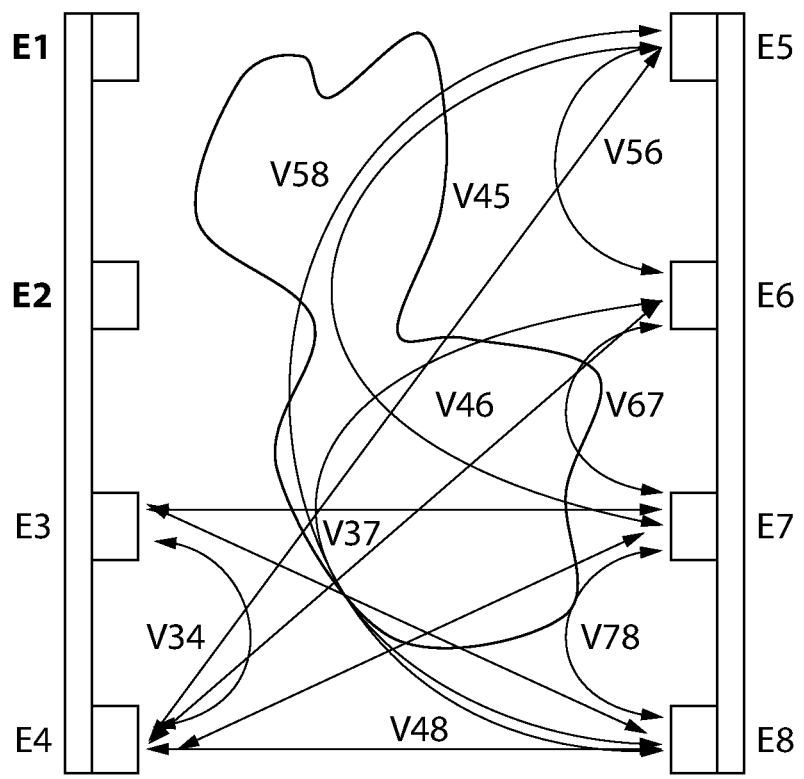
FIG. 7 shows an example signal transmission corresponding to a four-pole (8 electrode) configuration.

FIGS. 6A-6H show example configurations corresponding to the two-pole configuration shown on FIG. 5A. FIG. 7 depicts an example configuration corresponding to the four-pole configuration shown on FIG. 5B. Although FIGS. 5A, 5B, 6A-6H, and 7 show two and four-pole configurations, it should be understood that these configurations are for illustration purposes only. Additional EIT configurations, including different pole configurations and/or different electrode configurations, may be used to determine the oral health of a user via EIT. For example, other configurations may have additional pole-configurations and/or more or less electrodes within each pole-configuration.

As shown on FIG. 5A, a two-electrode (e.g., two-pole) configuration may be used in EIT. In a two-pole configuration, one pair of electrodes may be used both for signal emission and voltage measurement. In other words, in a two-pole configuration, a single electrode may act as an emitter and another single electrode may act as a receiver. In a two-pole configuration, electrodes may be larger than in four-pole configuration, for example, due to two-pole configurations being further affected by skin impedance.

As shown on FIG. 5B, a four-electrode (e.g., four-pole) configuration may be used in EIT. In a four-pole configuration, separate pairs of electrodes may be used for signal projection and voltage measurement. In other words, in a four-pole configuration, a pair (e.g., an adjacent pair) of electrodes may act as an emitter and another pair (e.g., an adjacent pair) of electrodes may act as a receiver.

FIGS. 6A-6H show example two-pole EIT electrode configurations using 8 electrodes. Using the example shown on FIGS. 6A-6H, electrical signals may be sent through the oral cavity 602 of a user (e.g., through the user's gingiva) via one or more of electrodes. FIG. 6A shows an example where electrode E1 is the electrode sending the electrical signal (electrical signals designated by a line delimited by an arrow). In FIG. 6A, each of the other electrodes (e.g. E2-E8) receive the electrical signal (e.g., each of the other electrodes receive the signal independently from each of the other electrodes) sent by E1. FIGS. 6B-6H show different configurations in which a different electrode (e.g., E2 for FIG. 6B) sends an electrical signal.

FIG. 7 shows an example four-pole configuration using 8 electrodes. The electrical signals may be sent through the oral cavity 702 of a user (e.g., through the user's gingiva) via electrodes E1-E8. FIG. 7 shows an example where electrodes E1 and E2 (E1/E2) send the electrical signal. FIG. 7 further shows example combinations of electrodes receiving the potential differences (e.g., voltage measurements) initiated by electrodes E1 and E2. For example, electrodes E6/E7, E7/E8, E8/E4, etc., may receive signals and/or take measurements upon E1/E2 sending an electrical signal. As described herein, the signals received by electrodes E6/E7, E7/E8, E8/E4 may be altered signals of E1 and E2.

Figure 8A:
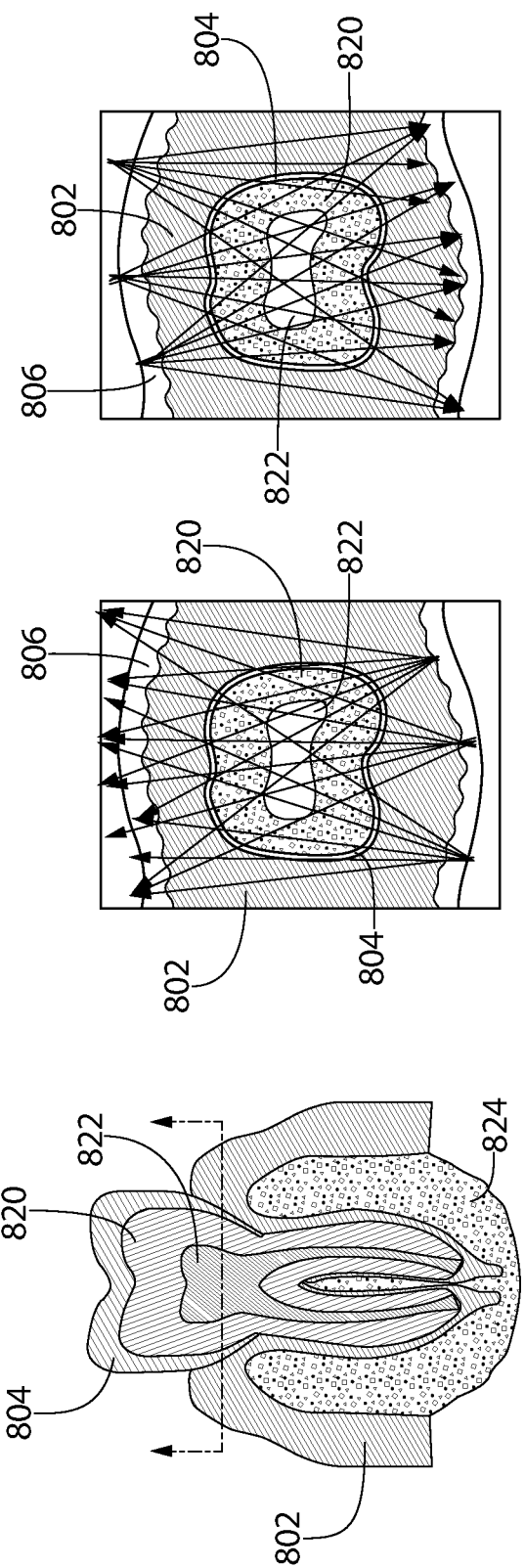
FIG. 8A shows example electrical signals being sent through a normal gingiva
Figure 8B:
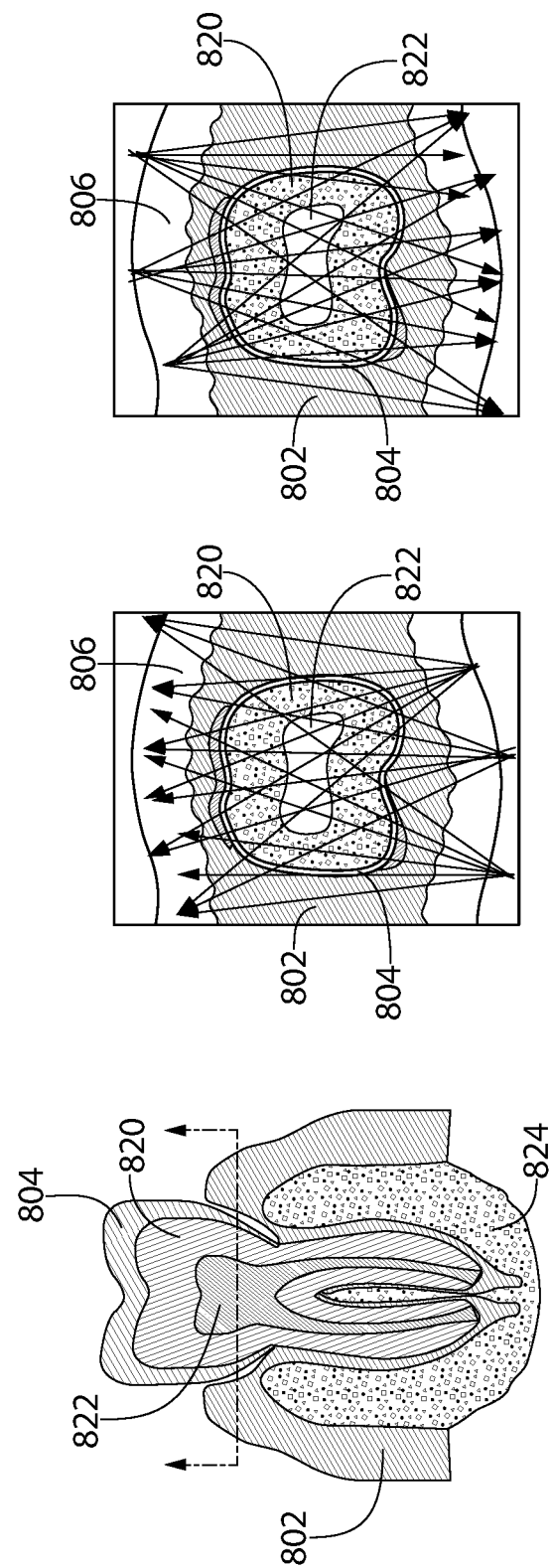
FIG. 8B shows example electrical signals being sent through an abnormal gingiva.

FIGS. 8A, 8B show example electrical signals (e.g., current) being sent through a normal gingiva (FIG. 8A) and an abnormal gingiva (FIG. 8B). As shown on FIGS. 8A, 8B, and described further herein, electrical signals may be sent from an electrode and received from one or more other electrodes. For normal and/or abnormal gingiva, the electrical signals may be sent through gingiva 802, tissue 806, enamel 804, dentin 820, pulp 822, bone 824, and the like. As shown on FIG. 8B, the electrical signals may be also be sent through a pocket 808. The electrical signals may be sent through one or more other tissue, fluids, or structures found in the oral cavity of a user, such as plaque, tartar, water, blood, etc. Based on the electrical signals sent through the oral cavity of the user, an EIT profile may be created, as described herein.

An EIT profile may be created for the example signals (e.g., electrical signals) that are sent and/or received (e.g., sent and/or received via electrodes), as shown on FIG. 8A. The EIT profile for the example shown on FIG. 8A may indicate that the gingiva is normal. The EIT profile for the example shown on FIG. 8B may indicate that the gingiva is abnormal. The EIT profile for the example shown on FIG. 8B may further indicate one or more of the abnormalities of the oral cavity (e.g., gingiva), which may include, for example, that the oral cavity has an abnormal pocket 808.

One or more gum health characteristics may be determined and/or monitored using the system and/or device described herein. For example, the system and device may be used to determine and/or monitor abnormal connective tissue changes, quantification of gingival crevicular fluid, early detection of periodontal pocket, gum volume change, periodontal bone loss, etc. The measurements (e.g., routine measurements) provided by the system and/or device provided herein may be used to identify the anatomy (e.g., micro-anatomy) and/or function of the gingiva. Such identification may be used for disease diagnosis (e.g., early disease diagnosis) and/or may be used to reduce the health risk, discomfort, and/or inconvenience to a user. Additionally, or alternatively, the system and/or device may be used to determine and/or monitor progressive periodontal and oral diseases.

As non-limiting examples, the system and/or device described herein may be used to provide quantitative information that may be used to determine and/or monitor the oral health of a user. For example, the system and/or device may be used to determine and/or monitor tissue (e.g., internal tissue) morphological changes, a concentration of gingival crevicular fluid, detection (e.g., early detection) of periodontal pocket, gum volume change, periodontal bone loss, and/or detection of tartar, calculus, and/or tissue firmness.

Figure 9:
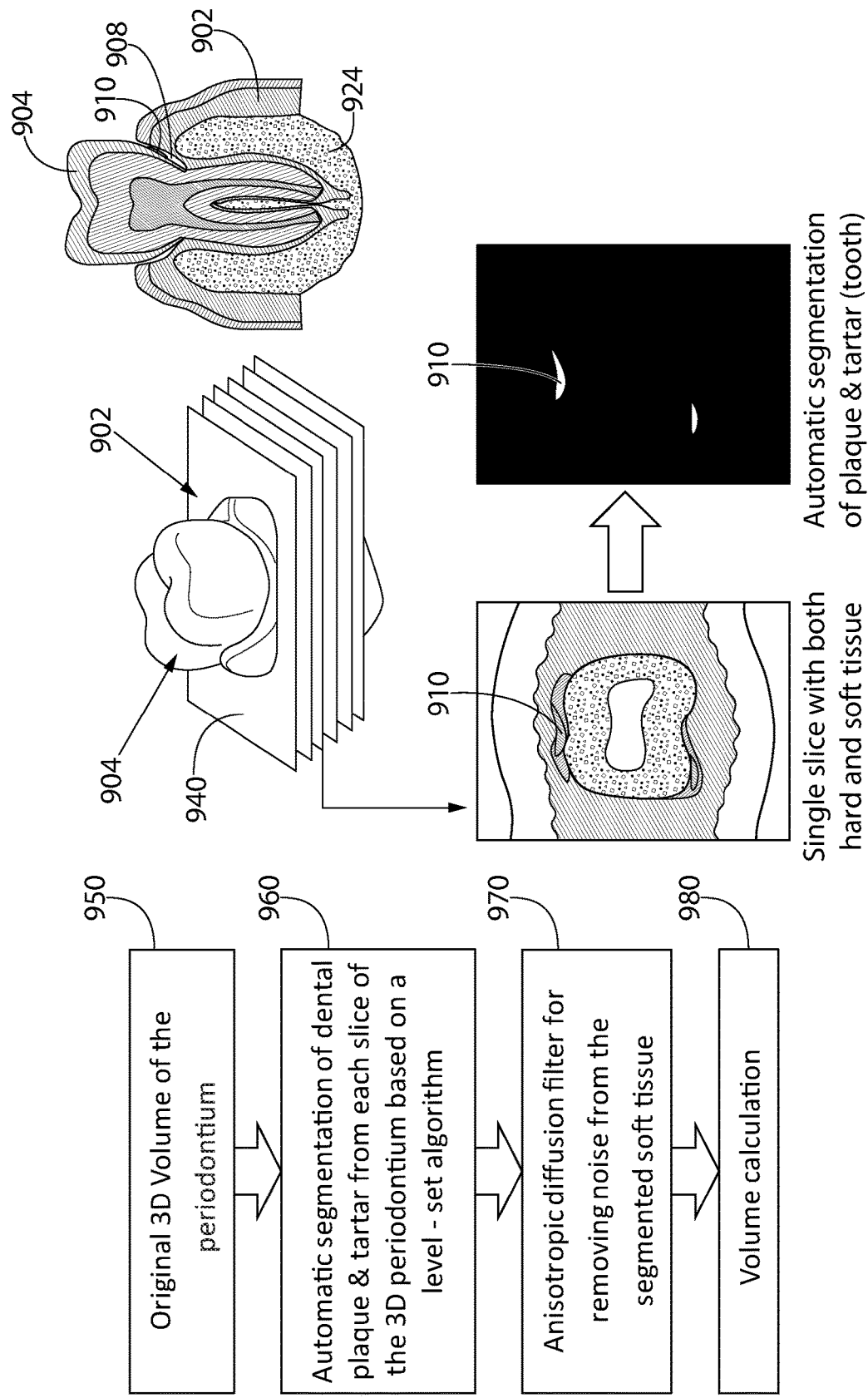
FIG. 9 shows an example volume calculation of plaque and/or tartar using EIT.

FIG. 9 shows an example volume calculation of plaque and tartar using EIT. The volume calculation may be performed using one or more slices 940 of EIT images. The volume calculation may be performed of hard tissue and/or soft tissue within the oral cavity using one or more slices 940 of EIT images. For example, as shown on FIG. 9, slices 940 of a user's volume calculations may be performed using one or more slices of a tooth (e.g., enamel 904), gingiva 902, plaque and tartar 910, a pocket 908, tissue 906, and bone 924.

The volume calculations may be used to determine and/or monitor whether a user's oral cavity includes normal gingiva or abnormal gingiva. For example, the volume calculations may be used to determine whether one or more abnormalities, such as plaque and/or tartar 910, a pocket 908, a loss of bone 924, etc., may be present within the oral cavity of a user. In addition to determining whether the oral cavity includes one or more abnormalities, the slices 940 of the EIT images may be used to determine the volume of the respective abnormality. For example, as shown on FIG. 9, the slices 940 of the EIT images may be used to determine the volume of plaque and/or tartar 910 within the oral cavity of a user.

An example process for determining the volume of plaque and/or tartar is provided on FIG. 9. For example, at 950, a volume, such as a 3-dimensional volume (e.g. an original 3D volume), of a user's periodontium may be determined. The 3-dimensional volume may be provided via one or more slices of the EIT image profiles. At 960, the plaque and/or tartar of the user may be segmented (e.g., automatically segmented). The plaque and/or tartar of the user may be segmented via one or more (e.g., each) of the slices of the 3-dimensional periodontium. The plaque and/or tartar of the user may be segmented via one or more of the slices of the 3-dimensional periodontium based on aa level-set algorithm. At 970, a filter (e.g., anisotropic diffusion filter) may be used. For example, a filter may be used to remove noise from the segmented tissue (e.g., soft tissue). In 980, the volume calculation of the plaque and/or tartar may be performed.

Figure 10:
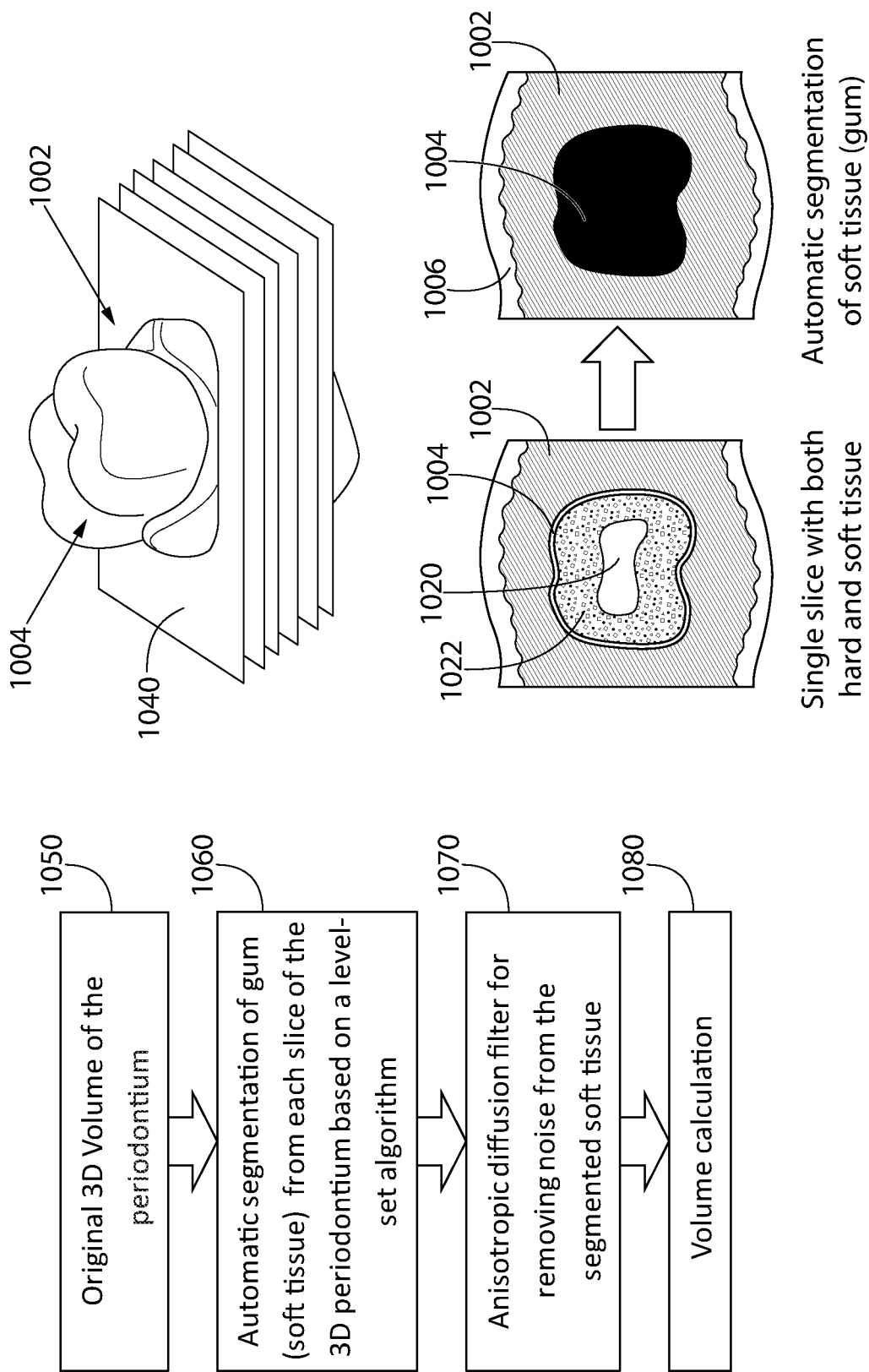
FIG. 10 shows an example volume calculation of a user's gingiva using EIT.

FIG. 10 shows an example volume calculation of the gingiva using EIT. The volume calculation may be performed using one or more slices 1040 of EIT images. The volume calculation may be performed of a hard tissue and/or a soft tissue within the oral cavity using one or more slices 1040 of EIT images. For example, as shown on FIG. 10, slices 1040 of a user's tooth (e.g., enamel 1004), gingiva 1002, plaque and tartar 1010, and tissue 1006 may be provided.

The volume calculations may be used to determine and/or monitor whether a user's oral cavity includes normal gingiva or abnormal gingiva. For example, the volume calculations may be used to determine whether one or more abnormalities, such as gingivitis and/or another gum disease, may be present within the oral cavity of a user. In addition to determining whether the oral cavity includes one or more abnormalities, the slices 1040 of the EIT images may be used to determine the volume of the respective abnormality. For example, as shown on FIG. 10, the slices 1040 of the EIT images may be used to determine the volume of a user's gingiva 1020 within the oral cavity of the user.

An example process for determining the volume of a user's gingiva (e.g., gingiva 1002) is provided on FIG. 10. At 1050, a volume, such as a 3-dimensional volume (e.g. an original 3D volume), of a user's periodontium may be determined. The 3-dimensional volume may be provided via one or more slices of the EIT image profiles. At 1060, the gingiva of the user may be segmented (e.g., automatically segmented). The gingiva of the user may be segmented via one or more (e.g., each) of the slices of the 3-dimensional periodontium. The gingiva of the user may be segmented via one or more of the slices of the 3-dimensional periodontium based on a level-set algorithm. At 1070, a filter (e.g., anisotropic diffusion filter) may be used. For example, a filter may be used to remove noise from the segmented tissue (e.g., soft tissue). In 1080, the volume calculation of the gingiva may be performed.

Figure 11:
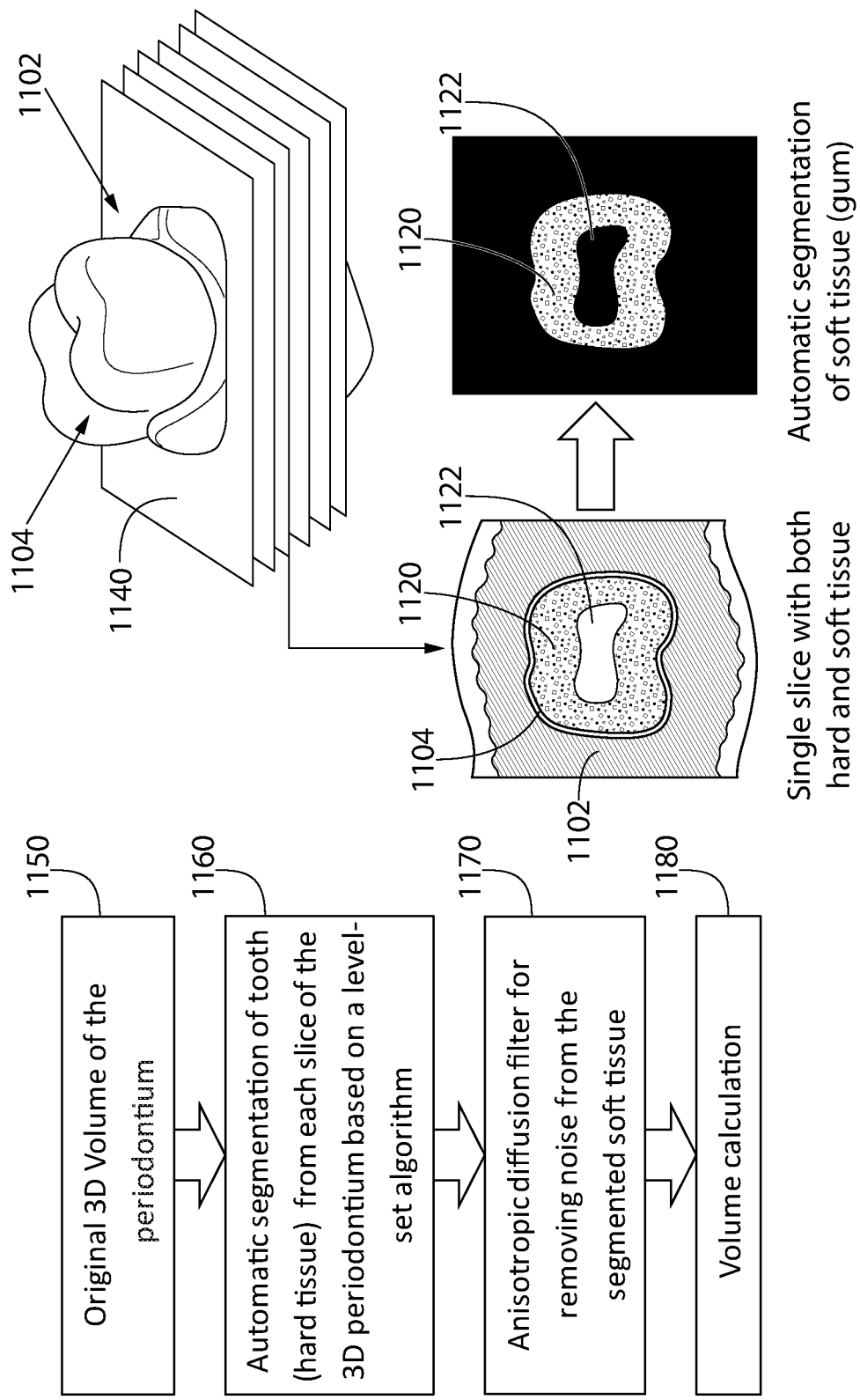
FIG. 11 shows an example volume calculation of bone and/or tooth using EIT.

FIG. 11 shows an example volume calculation of the bone and/or tooth using EIT. The volume calculation of the bone and/or tooth of a user may be used to determine if there is and/or has been any tooth and/or bone loss. The volume calculation may be performed using one or more slices 1140 of EIT images. As described herein, the volume calculation may be performed of a hard tissue and/or a soft tissue within the oral cavity using, for example, one or more slices 1140 of EIT images. For example, as shown on FIG. 11, slices 1140 of a user's tooth (e.g., enamel 1104, dentin 1120), gingiva 1102, pulp 1122, and tissue 1106 may be provided.

The volume calculations may be used to determine and/or monitor whether a user's oral cavity includes tooth and/or bone loss. For example, tooth and/or bone loss may be indicated by the volume of the user's tooth and/or bone having a less volume than previously determined. Additionally, or alternatively, tooth and/or bone loss may be indicated by the volume of the user's tooth and/or bone having a volume that is less than a tooth and/or bone of a user having characteristics that are similar to the user being monitored. In addition to determining whether the oral cavity includes one or more abnormalities, the slices 1140 of the EIT images may be used to determine the volume of the respective abnormality. For example, as shown on FIG. 11, the slices 1140 of the EIT images may be used to determine the amount of loss to a user's tooth and/or bone.

An example process for determining the volume of a user's tooth and/or bone is provided on FIG. 11. At 1150, a volume, such as a 3-dimensional volume (e.g. an original 3D volume), of a user's periodontium may be determined. The 3-dimensional volume may be provided via one or more slices of the EIT image profiles. At 1160, the tooth and/or bone of the user may be segmented (e.g., automatically segmented). The tooth and/or bone of the user may be segmented via one or more (e.g., each) of the slices of the 3-dimensional periodontium. The tooth and/or bone of the user may be segmented via one or more of the slices of the 3-dimensional periodontium based on a level-set algorithm. At 1170, a filter (e.g., anisotropic diffusion filter) may be used. For example, a filter may be used to remove noise from the segmented tissue (e.g., soft tissue). In 1180, the volume calculation of the tooth and/or bone may be performed.

Figure 12:
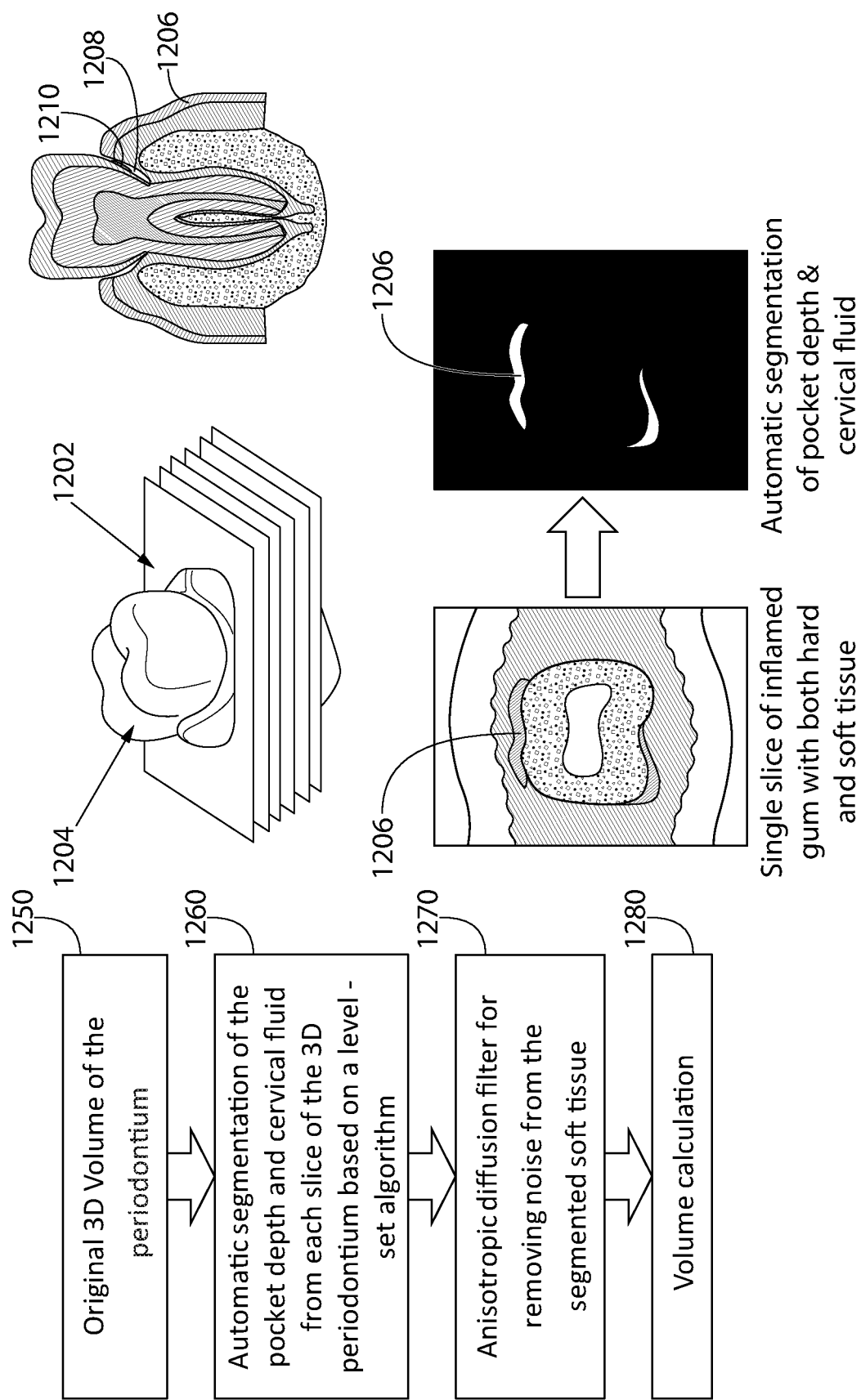
FIG. 12 shows an example volume calculation of cervical fluid and/or pocket depth using EIT.

FIG. 12 shows an example volume calculation of the cervical fluid and pocket depth using EIT. The volume calculation of the bone and/or tooth of a user may be used to determine if the amount of cervical fluid present within the oral cavity of a user and/or the depth of a pocket within the oral cavity of the user. The volume calculation may be performed using one or more slices 1240 of EIT images. As described herein, the volume calculation may be performed of a hard tissue and/or a soft tissue using, for example, one or more slices 1240 of EIT images. For example, as shown on FIG. 12, slices 1240 of a user's tooth (e.g., enamel 1204), pocket 1208, gingiva 1202, plaque and tartar 1210, and tissue 1206 may be provided.

The volume calculations may be used to determine and/or monitor the amount of cervical fluid and/or the depth of a pocket 1208 within a user's oral cavity. The amount of cervical fluid may be indicated as abnormal by the cervical fluid being more or less than a previous determination of the user, and/or by the cervical fluid being more or less than a cervical fluid measurement of a normal oral cavity, for example, of a user having characteristics that are similar to the user being monitored. The depth of the pocket 1208 may be indicated as abnormal by the pocket 1208 being different (e.g., larger) than a previous determination, and/or by the pocket depth being different (e.g., larger) than a pocket depth measurement of a normal oral cavity, for example, of user having characteristics that are similar to the user.

An example process for determining the volume of the cervical fluid and/or pocket depth within the oral cavity of a user is provided on FIG. 12. At 1250, a volume, such as a 3-dimensional volume (e.g. an original 3D volume), of a user's periodontium may be determined. The 3-dimensional volume may be provided via one or more slices of the EIT image profiles. At 1260, the cervical fluid and/or pocket depth of the user may be segmented (e.g., automatically segmented). The cervical fluid and/or pocket depth of the user may be segmented via one or more (e.g., each) of the slices of the 3-dimensional periodontium. The cervical fluid and/or pocket depth of the user may be segmented via one or more of the slices of the 3-dimensional periodontium based on a level-set algorithm. At 1270, a filter (e.g., anisotropic diffusion filter) may be used. For example, a filter may be used to remove noise from the segmented tissue (e.g., soft tissue). In 1280, the volume calculation of the tooth and/or bone may be performed.

Figure 13:
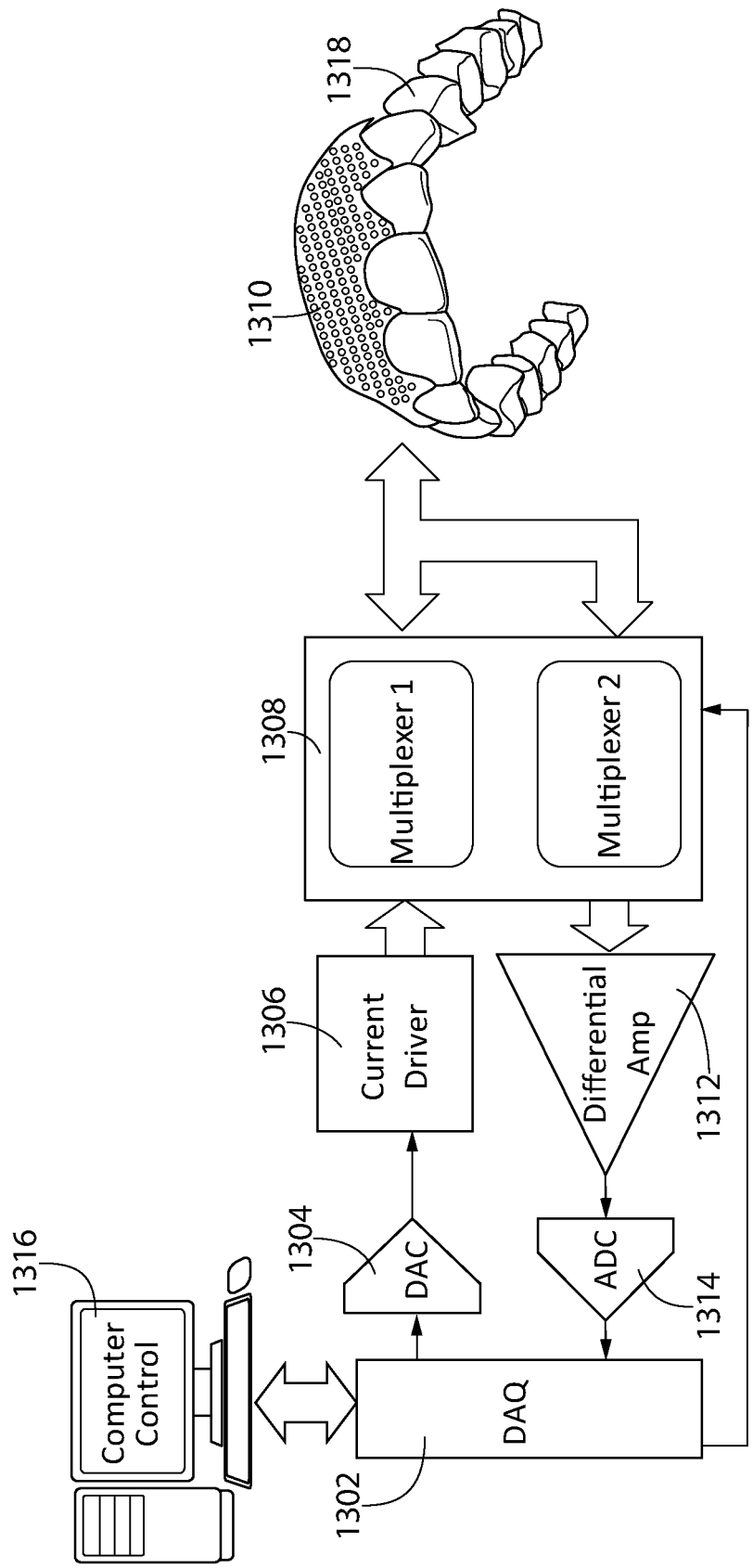
FIG. 13 shows an example system for determining the oral health of a user using EIT.

An example system 1300 for determining the oral health of a user using EIT, as described herein, is provided on FIG. 13. The system 1300 is configured to interface with an oral cavity 1318 of a user. For example, as provided on FIG. 13, one or more electrodes 1310 (e.g., an electrode array) may be placed upon the oral cavity 1318 of a user. The electrodes 1310 may be placed upon the oral cavity 1318 of a user via one or more configurations. For example, the electrodes 1310 may be placed upon the oral cavity 1318 of a user via a member (e.g., a flexible member) that physically is applied to the oral cavity 1318 of the user. The member may be applied to the oral cavity 1318 (e.g., the gingiva of the user) directly or indirectly. In an example, the member may be configured to be adhesively applied to the oral cavity of the user. In other examples, a device, such as a mouthpiece, may be used to apply the member to the oral cavity of the user.

System 1300 may include one or more devices. For example, system 1300 may include a signal processing circuit. The signal processing circuit of System 1300 may include computer control 1316, a data acquisition (DAQ) device 1302, a digital to analog converter (DAC) 1306, a current driver 1306, a multiplexer, such as one or more multiplexers 1308, an amplifier, such as differential amplifier 1312, and/or an analog to digital converter (ADC) 1314. One or more of the devices shown on FIG. 13 may include a processor, software, and/or a combination of processor and software, as understood by those of skill in the art. The signal processing circuit may be used to process data, transmit data, receive data, and the like.

In an example, DAQ device 1302 may be used to process the measurements provided by the electrodes 1310 and/or to convert the measurements to be provided to the computer control 1316. The computer control 1316 may receive the measurements from the DAQ 1302. Using the measurements, the computer control 1316 may create images (e.g., tomographic images). The computer control 1316 may create the images using software configured to create the tomographic images based on the received measurements.

Current driver 1306 may be used to produce the electrical signal (e.g., current) that will be sent (e.g., injected) into the oral cavity of the user. As shown on FIG. 13, the current driver 1306 may be used to send the electrical signal to the oral cavity of the user via one or more multiplexers 1308. Multiplexers 1308 may be used to receive one or more electrical signals from the current driver 1306 and send an electrical signal (e.g., a single electrical signal derived from the one or more signals received by the multiplexer 1308) to the electrodes 1310 applied to the oral cavity of the user. Multiplexer 1308 may also, or alternatively, be used to receive one or more signals from the electrodes 1310. Upon receiving the one or more electrical signals from the electrodes 1310, multiplexer 1308 may provide a signal (e.g., a single signal) of the many signals derived from the electrodes 1310. The multiplexer 1308 may send the electrical signal to the differential amplifier 1312.

The differential amplifier 1312 may be used to amplify the signals provided by the multiplexers 1308. For example, the differential amplifier 1312 may be used to amplify the potential differences (voltages) received from the electrodes. Differential amplifier 1312 may be used because the signals received from multiplexers 1308 are weak and/or of small magnitude. The differential amplifier 1312 may pass the amplified signal to ADC 1314.

ADC 1314 may be used to receive analog signals (e.g., analog voltages) from the differential amplifier 1312 and/or may convert the voltage to a digital number. For example, the digital number may represent the magnitude of the electrical signal (e.g., the voltage). The DAC 1304 may perform the reverse function of the ADC 1314. For example, the ADC 1314 may be used to convert a digital signal (e.g., a digital signal derived from computer control 1316) into an analog signal.

Figure 14:
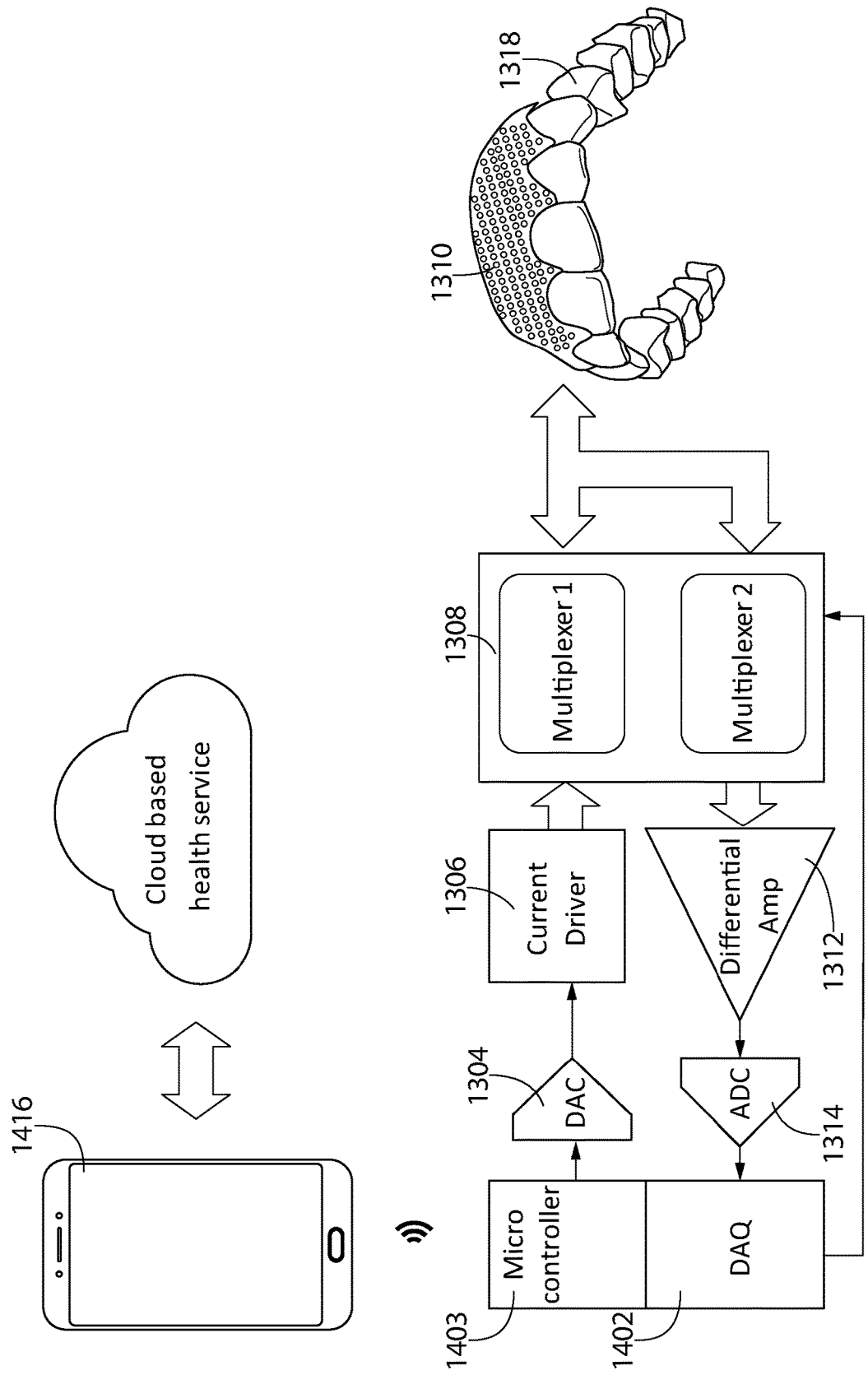
FIG. 14 shows another example system for determining the oral health of a user using EIT.

FIG. 14 shows another example system 1400 for determining the oral health of a user using EIT. System 1400 may include one or more devices. System 1400 may have one or more (e.g., including all) devices that are similar, or different, than system 1300. For reference purposes, like devices of system 1400 and system 1300 may use the same numbering scheme on FIGS. 14 and 13, respectively.

System 1400 may include a signal processing circuit. The signal processing circuit of System 1400 may include computing device 1416, Microcontroller 1403, data acquisition (DAQ) device 1402, a digital to analog converter (DAC) 1306, a current driver 1306, a multiplexer, such as one or more multiplexers 1308, an amplifier, such as differential amplifier 1312, and/or an analog to digital converter (ADC) 1314. One or more of the devices shown on FIG. 14 may include a processor, software, and/or a combination of processor and software, as understood by those of skill in the art. The signal processing circuit may be used to process data, transmit data, receive data, and the like.

System 1400 is configured to interface with an oral cavity 1318 of a user. For example, as provided on FIG. 13, one or more electrodes 1310 (e.g., an electrode array) may be placed upon the oral cavity 1318 of a user. The electrodes may be placed upon the oral cavity 1318 of a user via one or more configurations. For example, the electrodes 1310 may be placed upon the oral cavity 1318 of a user via a member (e.g., a flexible member) that may be physically applied to the oral cavity 1318 of the user. The member may be applied to the oral cavity 1318 (e.g., the gingiva of the user) directly or indirectly. In an example, the member may be configured to be adhesively applied to the oral cavity of the user. In other examples, a device, such as a mouthpiece, may be used to apply the member to the oral cavity of the user.

As described herein, example system 1400 may include a computing device 1416. Computing device 1416 may be used for receiving, sending, and/or processing of information. For example, computing device 1416 may send information (e.g., EIT profile information, data indicative of one or more signals, user oral care characteristics, etc.) to a server. For example, computing device 1416 may send information to a cloud-based server. The computing device 1416 may send information to a server for further processing of the information and/or for storage of the information. Although computing device is shown as a mobile phone on FIG. 14, computing device 1416 may be a tablet, a smartphone, a laptop, or any computing device used for receiving, sending, and/or processing information.

System 1400 may include DAQ 1402 and/or Microcontroller 1403. DAQ 1402 and/or Microcontroller 1403 may be a single device (as shown in the example depicted on FIG. 14), or DAQ 1402 and/or Microcontroller 1403 may be separate devices. DAQ device 1402 may be used to process the measurements provided by the electrodes 1310 and/or to convert the measurements to be provided to the computing device 1416. Microcontroller 1403 may be used to control one or more of the components of system 1400. Also, or alternatively, microcontroller 1403 may be used to communicate with computing device 1416.

Computing device 1416 may receive information (e.g., measurements) from DAQ 1402 and/or from microcontroller 1403. For example, computing device 1416 may receive information (e.g., measurements) from DAQ 1402 and/or from microcontroller 1403 using one or more communications 1420. For example, computing device 1416 may receive information (e.g., measurements) from DAQ 1402 and/or from microcontroller 1403 via a wire, or wirelessly (e.g., via Bluetooth, Wi-Fi, etc.). Computing device 1416 may process the received information and/or computing device 1416 may create images (e.g., tomographic images). In other examples, computing device 1416 may transmit a portion, or all, of the information to an external source 1418 for processing the information and/or creating the images (e.g., the tomographic images). Examples of external sources 1418 may include a server, another computer, the cloud, etc. Tomographic images may be created using software configured to create the tomographic images based on the received measurements.

Figure 15:
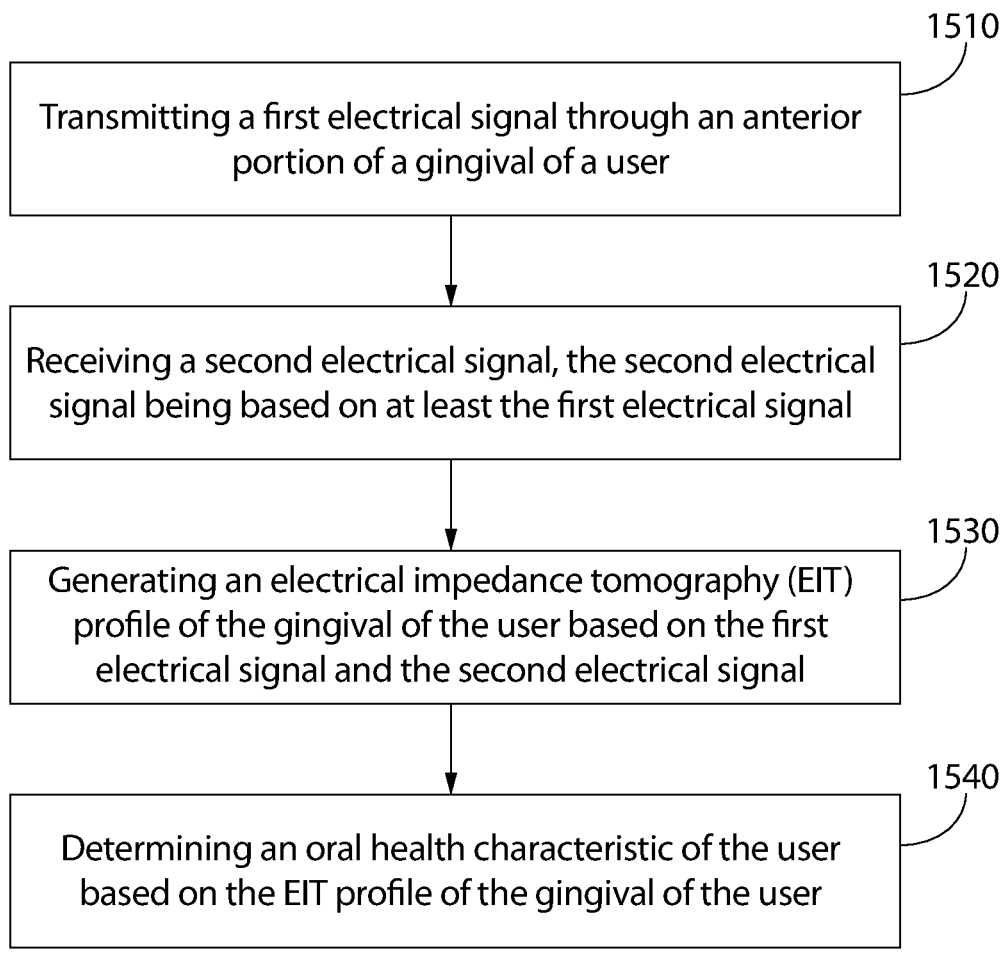
FIG. 15 shows an example procedure for determining an oral health characteristic using EIT.

FIG. 15 shows an example procedure for determining an oral health characteristic using EIT. For example, the presence of at least one of a periodontal pocket, a gum volume change, a periodontal bone loss, an abnormal connective tissue change, and a quantification of a gingival crevicular fluid may be determined. At 1510, a first electrical signal may be transmitted, for example, via an electrode. The first electrical signal may be transmitted through an anterior portion of a gingiva of a user. The electrode may be housed on a flexible membrane and/or the flexible membrane may be positioned upon a mouthpiece.

At 1520, a second electrical signal may be received, for example, via an electrode. In an example where the electrical signal is sent through an anterior portion of a gingiva, the receiving electrode may be positioned upon the posterior of the gingiva, or vice-versa. The second electrical signal may be an altered first electrical signal. The second electrical signal may be based on at least the first electrical signal.

At 1530, an electrical impedance tomography (EIT) profile of the gingiva of the user may be generated. The EIT profile may be generated by the oral care device (e.g., the mouthpiece or one or more devices coupled to the mouthpiece). The EIT profile may be generated by an external device, such as a smartphone, tablet, laptop, computer, or the like. The EIT profile may be generated by one or more servers (such as the cloud). The EIT profile may be based on the first electrical signal and/or the second electrical signal. The EIT profile may be displayed via a display device. The display device may be the same device that generates the EIT profile, or another device.

At 1540, an oral health characteristic of the user may be determined and/or monitored. The oral health characteristic may be based on the EIT profile of the gingiva of the user. The oral health characteristic of the user may be determined based on one or more EIT profiles. For example, it may be determined if the gingiva of the user is normal or abnormal based on a single EIT profile of the user. The oral health characteristic may be determined based on more than one EIT profile (e.g., based on a comparison of the user's EIT profile with previously observed/generated EIT profiles), such as via a pool of EIT profiles. The more than one EIT profile may be EIT profiles of the user, in an example. In other examples, the more than one EIT profile may be EIT profiles of users other than the user.

The oral health characteristic that may be determined and/or monitored may include one or more of abnormal connective tissue changes, quantification of gingival crevicular fluid, early detection of periodontal pocket, gum volume change, periodontal bone loss, etc. The measurements (e.g., routine measurements) provided by the system and/or device provided herein may be used to identify the anatomy (e.g., micro-anatomy) and/or function of the gingiva. Such identification may be used for disease diagnosis (e.g., early disease diagnosis) and/or may be used to reduce the health risk, discomfort, and/or inconvenience to a user. Additionally, or alternatively, the system and/or device may be used to determine and/or monitor progressive periodontal and oral diseases.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A system comprising:
    an oral care device comprising:
        a mouthpiece;
        a first flexible membrane coupled to the mouthpiece;
        a first electrode configured to transmit a first signal through a gingiva of a user to cause an altered first signal, the first electrode housed on the first flexible membrane;
        a second flexible membrane coupled to the mouthpiece;
        a second electrode configured to receive the altered first signal, the second electrode housed on the second flexible membrane;
        a signal processing circuit comprising at least a multiplexor; and
        a processor configured at least to:
            receive from the oral care device data indicative of the first signal and the altered first signal; and
            generate an electrical impedance tomography (EIT) profile of the gingiva of the user based on the data indicative of the first signal and the altered first signal;
        wherein the first flexible membrane is configured to be placed upon one of an anterior portion or a posterior portion of the gingiva of the user, and the second flexible membrane is configured to be placed upon another one of the anterior portion or the posterior portion of the gingiva; and
        wherein the processor is further configured to:
            determine the EIT profile of the gingiva of the user based on a potential difference between the first signal and the altered first signal;
            determine the oral health characteristic of the user based on the EIT profile of the gingiva of the user;
            determine a three-dimensional volume of the user's periodontium, the three-dimensional volume comprising one or more slices of an EIT profile image;
            segment the user's plaque and tartar from the one or more slices of the EIT profile image to produce segmented tissue;
            apply a filter to the segmented tissue to remove noise from the segmented tissue; and
            determine a volume of the user's plaque and tartar from the filtered segmented tissue.

2. The system of claim 1, wherein the processor is further configured to determine an oral health characteristic of the user based on a comparison of the EIT profile of the gingiva of the user and one or more other EIT profiles.

3. The system of claim 1, wherein the determination of the oral health characteristic of the user further comprises a determination of a presence of at least one of a periodontal pocket, a gum volume change, a periodontal bone loss, an abnormal connective tissue change, or a quantification of a gingival crevicular fluid.

4. The system of claim 1 wherein the processor is further configured such that the filter is an anisotropic diffusion filter.

5. A method for determining an oral heath characteristic of a user comprising:
    providing a mouthpiece, the mouthpiece having a first flexible membrane, a second flexible membrane, a first electrode housed on the first flexible membrane, a second electrode housed on the second flexible membrane, and a signal processing circuit having a multiplexor, the first flexible membrane configured to be placed upon one of an anterior portion or a posterior portion of a gingiva of the user, and the second flexible membrane is configured to be placed upon another one of the anterior portion or the posterior portion of the gingiva;
    transmitting a first electrical signal through the gingiva of a user to cause an altered first signal via the first electrode;
    receiving the altered first signal via the second electrode;
    generating data indicative of the first signal and the altered first signal;
    generating an electrical impedance tomography (EIT) profile of the gingiva of the user based on the data indicative of the first signal and the altered first signal;
    determining the oral health characteristic of the user based on the EIT profile of the gingiva of the user;
    determining a three-dimensional volume of the user's periodontium, the three-dimensional volume comprising one or more slices of an EIT profile image;
    segmenting the user's plaque and tartar from the one or more slices of the EIT profile image to produce segmented tissue;
    applying a filter to the segmented tissue to remove noise from the segmented tissue; and
    determining a volume of the user's plaque and tartar from the filtered segmented tissue.

6. The method of claim 5, wherein the determining the oral health characteristic of the user further comprises determining a presence of at least one of a periodontal pocket, a gum volume change, a periodontal bone loss, an abnormal connective tissue change, or a quantification of a gingival crevicular fluid.

7. The method of claim 5 wherein the first electrode forms part of a first electrode array and the second electrode forms part of a second electrode array.

8. The method of claim 5, wherein determining the oral health characteristic of the user comprises comparing the EIT profile of the gingiva of the user and one or more other EIT profiles.

9. The method of claim 5, wherein the filter is an anisotropic diffusion filter.

\* \* \* \* \*